US010533207B2

(12) United States Patent
Jung et al.

(10) Patent No.: US 10,533,207 B2
(45) Date of Patent: Jan. 14, 2020

(54) BIOACTIVITY TESTING STRUCTURE FOR SINGLE CELL TRACKING USING GELLING AGENTS

(71) Applicant: QuantaMatrix Inc., Seoul (KR)

(72) Inventors: Yong-Gyun Jung, Seoul (KR); Eun Guen Kim, Gunpo-si (KR); Jung Heon Yoo, Yongin-si (KR); Kyung-Ock Park, Ansan-si (KR); Sunghoon Kwon, Seoul (KR); Jungil Choi, Seoul (KR); Hee jin Kim, Seoul (KR); Sung Weon Ryoo, Yongin-si (KR); Haeun Kim, Iksan-si (KR); Hyeon Ju Jeoung, Chuncheon-si (KR); Eun Hee Lee, Cheongju-si (KR); Hyejin Kim, Cheongju-si (KR)

(73) Assignee: QUANTAMATRIX INC., Seoul (KR)

( * ) Notice: Subject to any disclaimer, the term of this patent is extended or adjusted under 35 U.S.C. 154(b) by 112 days.

(21) Appl. No.: 15/518,668

(22) PCT Filed: Oct. 16, 2014

(86) PCT No.: PCT/KR2014/009755
§ 371 (c)(1),
(2) Date: Apr. 12, 2017

(87) PCT Pub. No.: WO2016/060301
PCT Pub. Date: Apr. 21, 2016

(65) Prior Publication Data
US 2017/0233786 A1 Aug. 17, 2017

(30) Foreign Application Priority Data
Oct. 16, 2014 (KR) .......................... 10-2014-0139700

(51) Int. Cl.
C12M 1/00 (2006.01)
C12M 3/00 (2006.01)
(Continued)

(52) U.S. Cl.
CPC ................. *C12Q 1/18* (2013.01); *C12M 1/14* (2013.01); *C12M 1/16* (2013.01); *C12M 1/18* (2013.01);
(Continued)

(58) Field of Classification Search
CPC combination set(s) only.
See application file for complete search history.

(56) References Cited

U.S. PATENT DOCUMENTS 5,652,142 A * 7/1997 Barker .................... C12M 25/04
422/536
6,416,969 B2 * 7/2002 Matsumura .............. C12Q 1/04
435/283.1
(Continued)

FOREIGN PATENT DOCUMENTS

CN 1039432 C 8/1998
EP 2987851 A1 2/2016
(Continued)

OTHER PUBLICATIONS

International Search Report of PCT/KR2014/009755, dated Jul. 14, 2015, English transiation.
(Continued)

Primary Examiner — Nathan A Bowers
(74) Attorney, Agent, or Firm — STIP Law Group, LLC

(57) ABSTRACT

The present invention relates to a novel bioactivity testing structure for single cell tracking using a gelling agent and a bioactivity testing system including the testing structure. The present invention also relates to bioactivity testing, drug susceptibility testing, antibiotic screening, and diagnostic
(Continued)

methods using the testing structure. The bioactivity testing structure of the present invention enables very rapid and simple drug susceptibility testing of bacteria, particularly *Mycobacterium tuberculosis*, drug screening, and bacterial diagnosis. Particularly, the use of the testing structure enables DST and diagnosis of bacteria only by pretreatment without the need to concentrate human sputum samples irrespective of inoculum effect, ensuring rapid, accurate, and simple testing compared to conventional tuberculosis diagnosis or DST systems. In addition, the testing structure of the present invention simultaneously enables the diagnosis and drug susceptibility testing of tuberculosis. Therefore, the present invention provides an effective alternative to the prior art.

28 Claims, 13 Drawing Sheets

(51) Int. Cl.
    *C12Q 1/18*     (2006.01)
    *C12Q 1/02*     (2006.01)
    *C12M 1/18*     (2006.01)
    *C12M 1/12*     (2006.01)
    *C12M 1/32*     (2006.01)
    *C12M 1/16*     (2006.01)
    *C12M 1/14*     (2006.01)
    *C12M 1/34*     (2006.01)
    *C12M 1/22*     (2006.01)
    *C12Q 1/04*     (2006.01)

(52) U.S. Cl.
    CPC .......... *C12M 23/10* (2013.01); *C12M 23/12* (2013.01); *C12M 23/20* (2013.01); *C12M 23/22* (2013.01); *C12M 25/14* (2013.01); *C12M 29/04* (2013.01); *C12M 29/26* (2013.01); *C12M 41/46* (2013.01); *C12Q 1/02* (2013.01); *C12Q 1/04* (2013.01); *G01N 2800/26* (2013.01)

(56) References Cited

U.S. PATENT DOCUMENTS

| | | | |
|---|---|---|---|
| 2004/0132218 A1* | 7/2004 | Ho .................. | B01L 3/5025 436/524 |
| 2005/0281711 A1* | 12/2005 | Testa ................ | B01L 3/508 422/400 |
| 2006/0194320 A1* | 8/2006 | Bushnaq-Josting ... | C12M 23/16 435/373 |
| 2010/0112690 A1* | 5/2010 | Eddington .......... | C12M 23/12 435/374 |
| 2011/0159522 A1* | 6/2011 | Kamm ............... | C12Q 1/02 435/7.21 |
| 2013/0196364 A1 | 8/2013 | Kwon et al. | |
| 2014/0057311 A1* | 2/2014 | Kamm ............... | B01L 3/502753 435/29 |
| 2014/0080206 A1* | 3/2014 | Dahan ............... | B01L 3/502753 435/288.7 |
| 2017/0267961 A1* | 9/2017 | Hung ................. | C12M 29/14 |

FOREIGN PATENT DOCUMENTS

| | | |
|---|---|---|
| JP | 2009513160 A | 4/2009 |
| KR | 1020050088124 A | 3/2007 |
| KR | 1020120115938 B1 | 7/2013 |
| KR | 1020130043014 A | 8/2013 |
| KR | 1020130089619 A | 8/2013 |
| KR | 101446526 B1 | 10/2014 |
| KR | 1020140053582 B1 | 10/2014 |

OTHER PUBLICATIONS

Office Action from the European Patent Office, dated Jun. 20, 2018.
Office action from China National Intellectual Property Administration of 2014800826594, dated Apr. 1, 2019.
Chinese Search Report of 2014800826594, dated Mar. 21, 2019.

* cited by examiner

[Fig. 1]
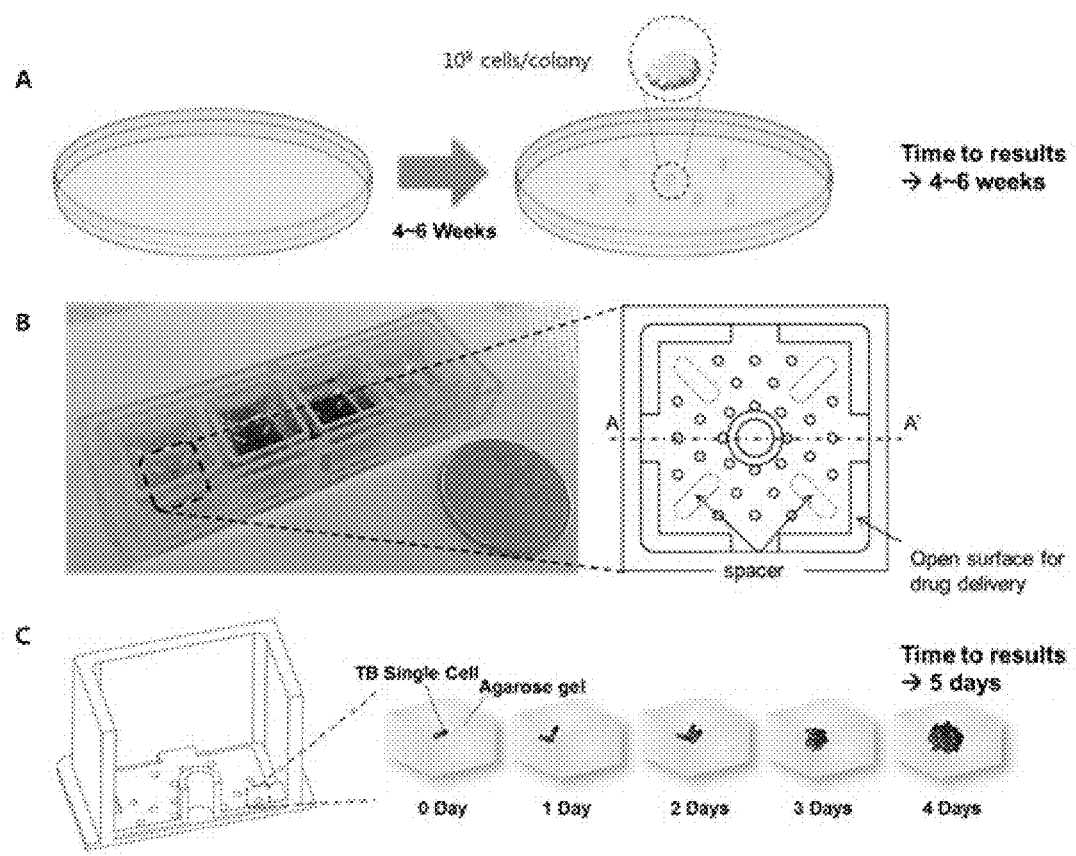

[Fig. 2a]
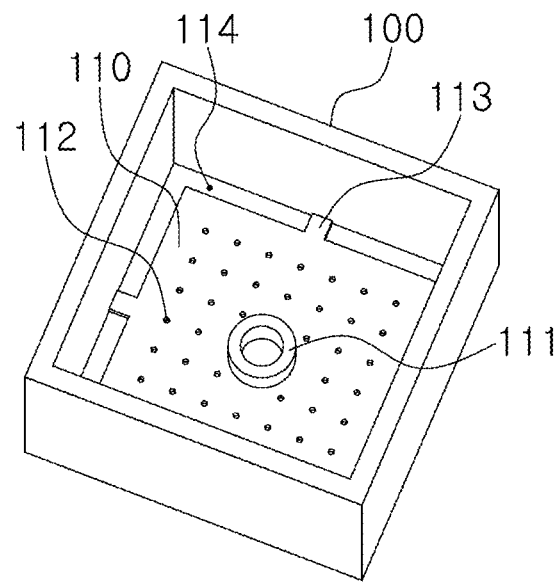
[Fig. 2b]
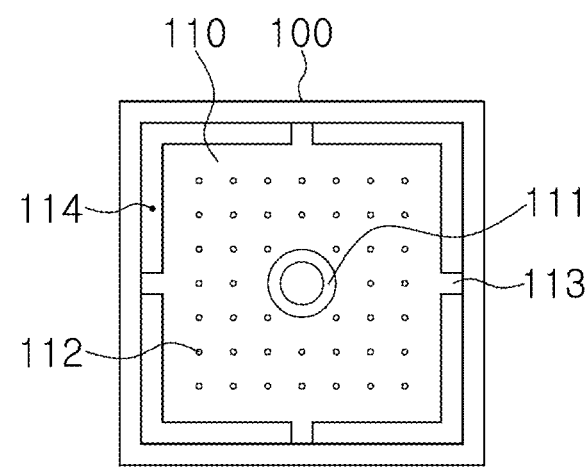

[Fig. 3a]
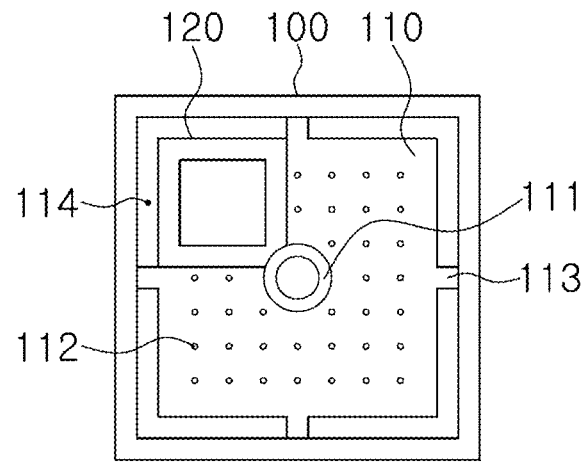
[Fig. 3b]
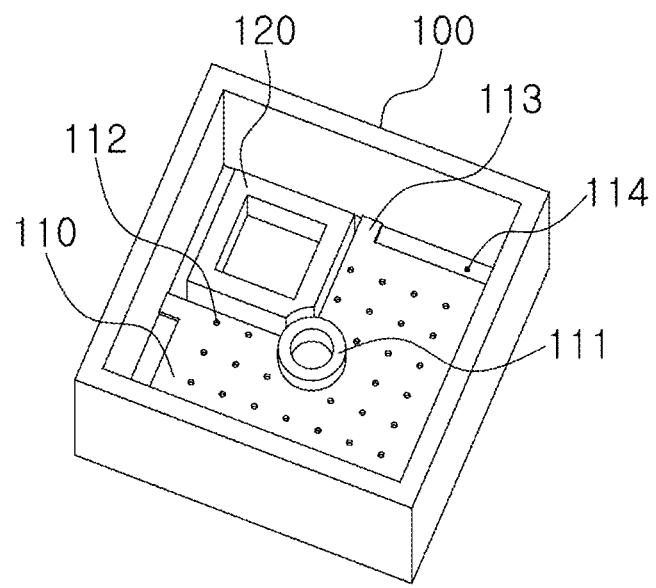

[Fig. 4]
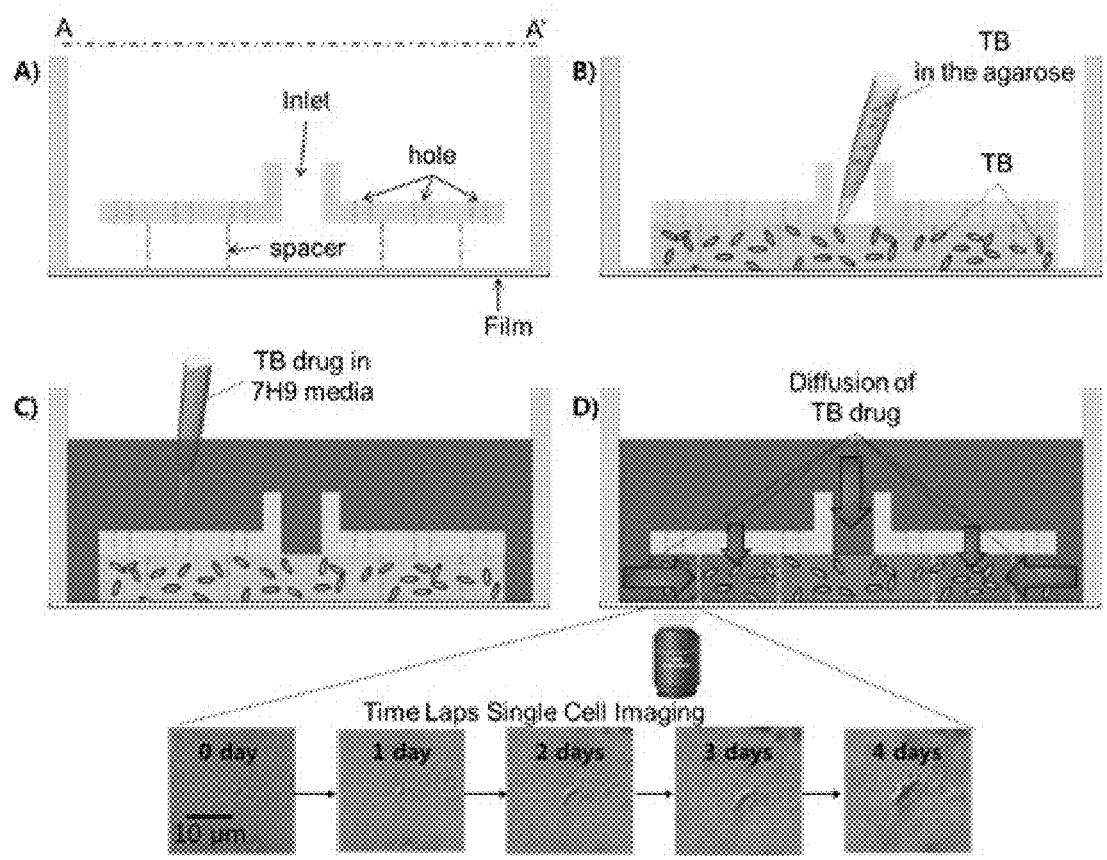

[Fig. 5]
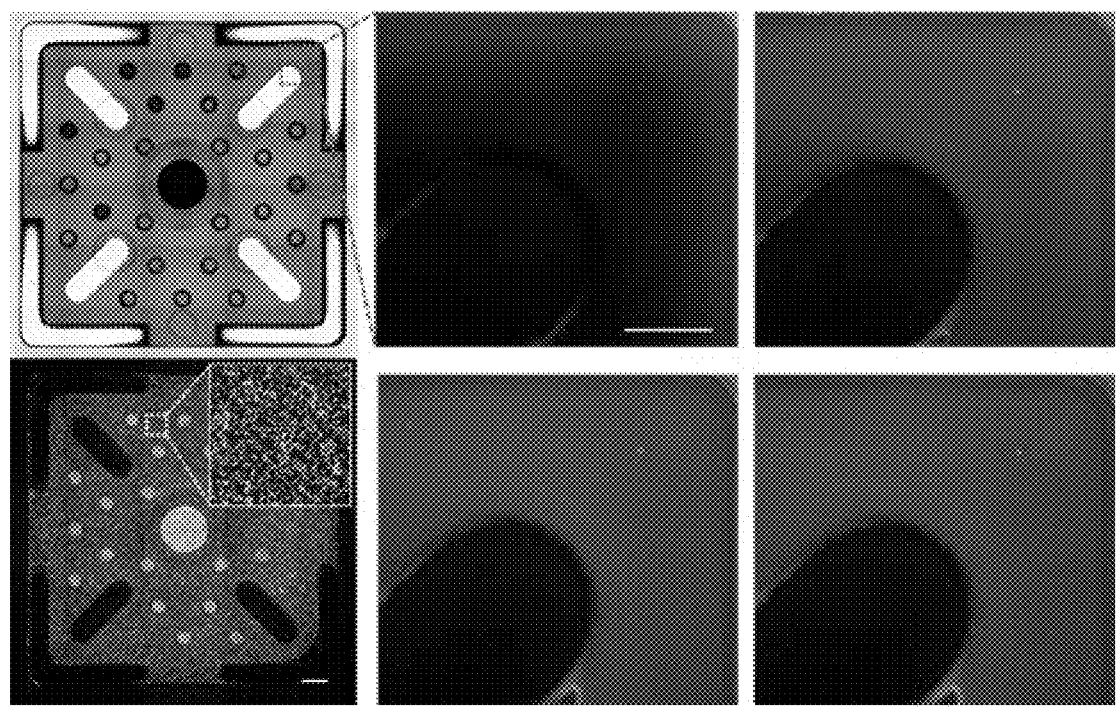

[Fig. 6]
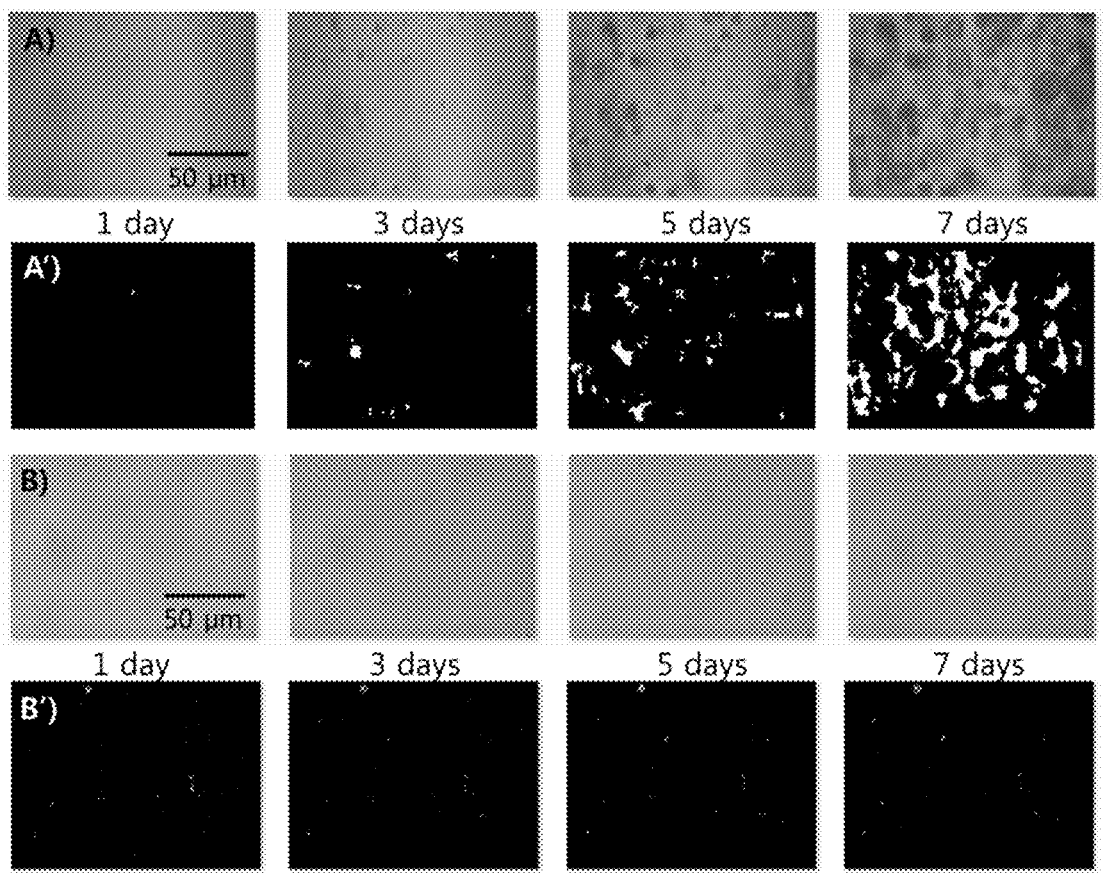

[Fig. 7]
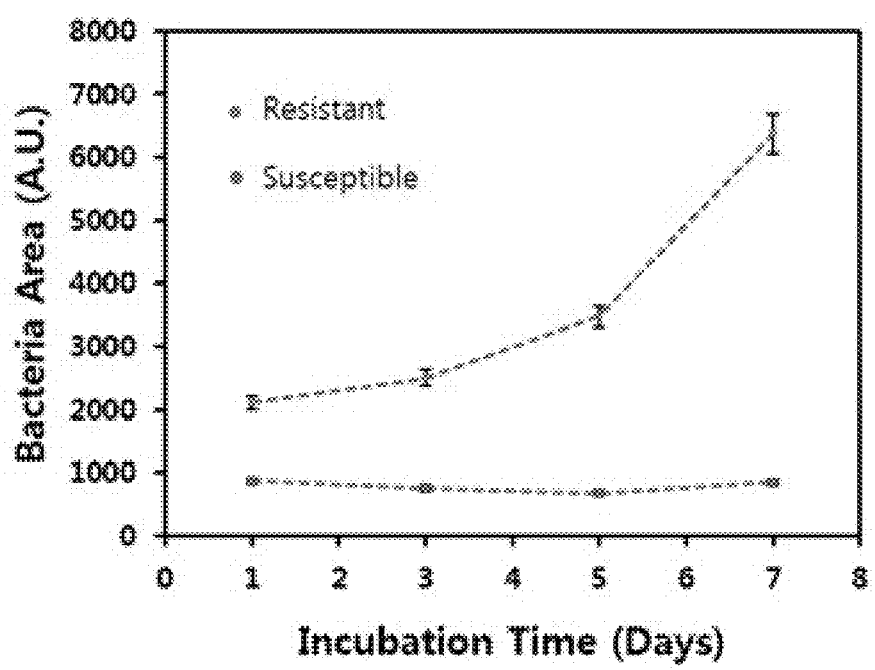

[Fig. 8]
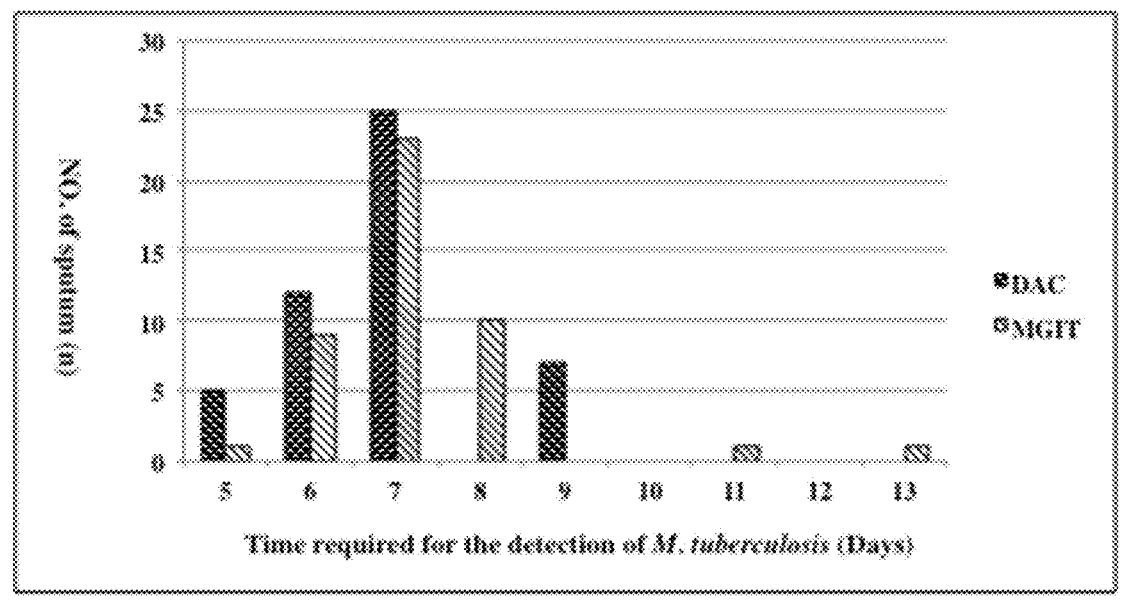
[Fig. 9]
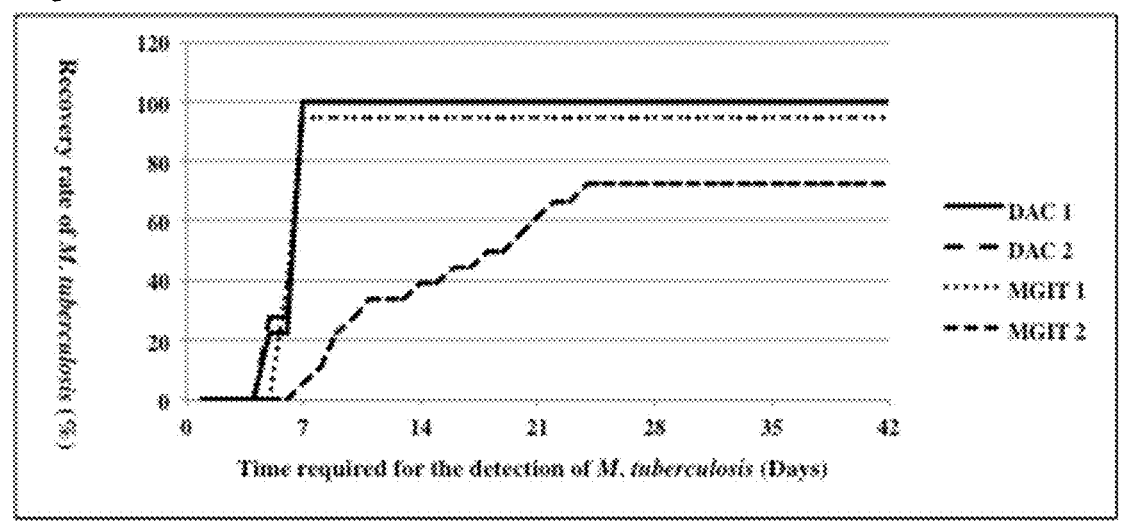

[Fig. 10]
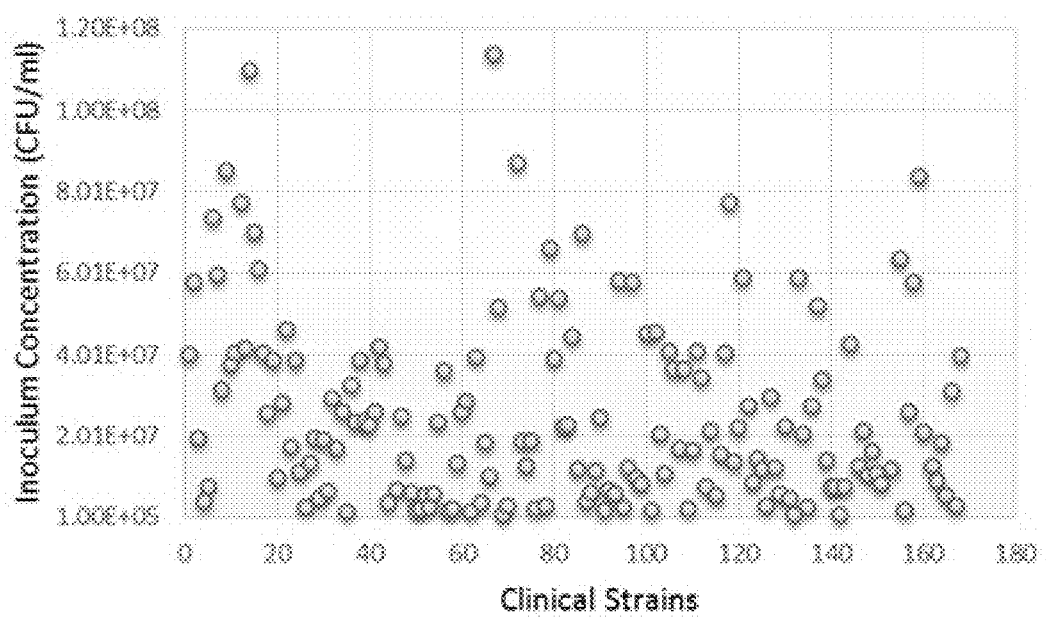

[Fig. 11]
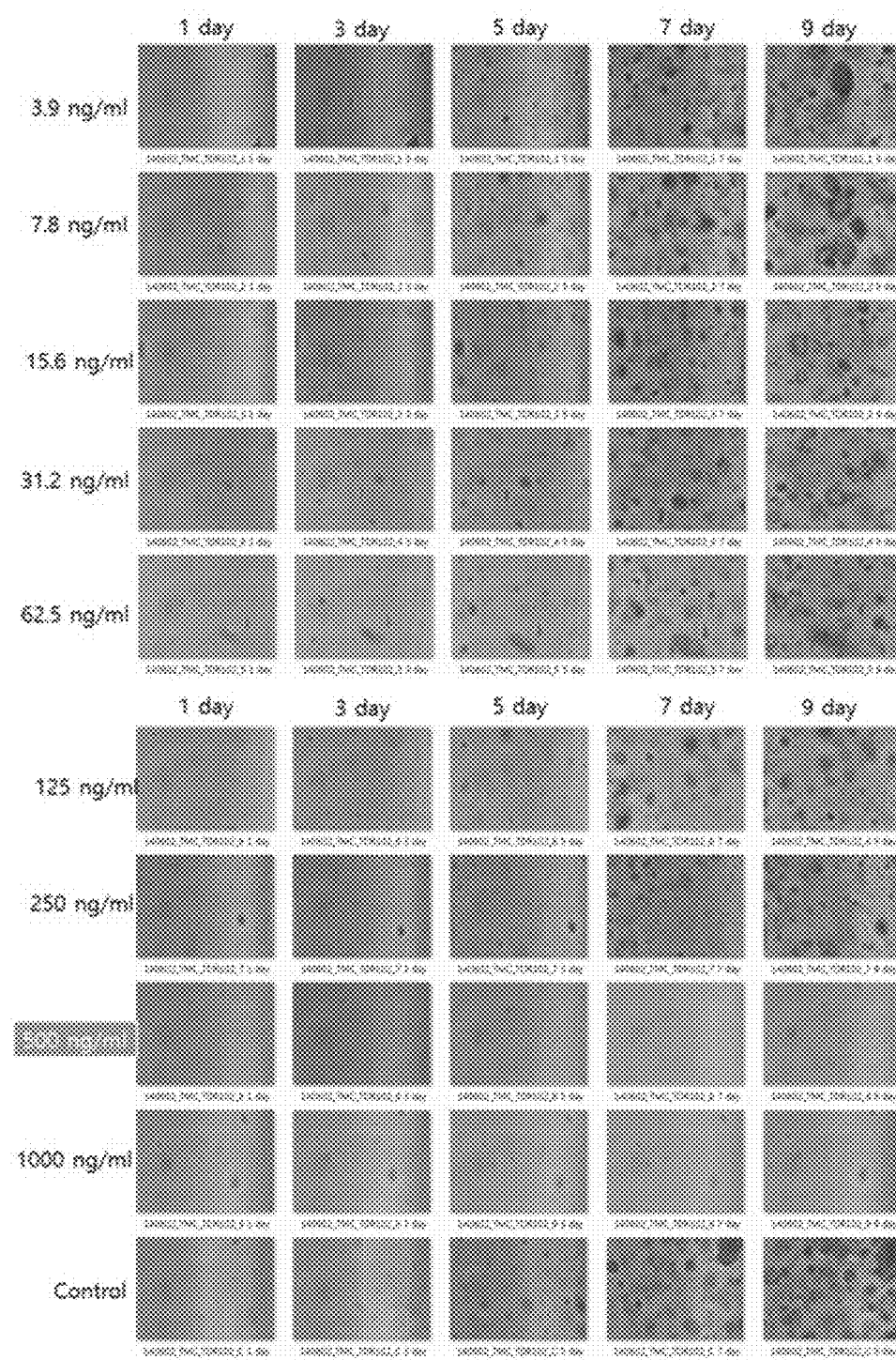

[Fig. 12]
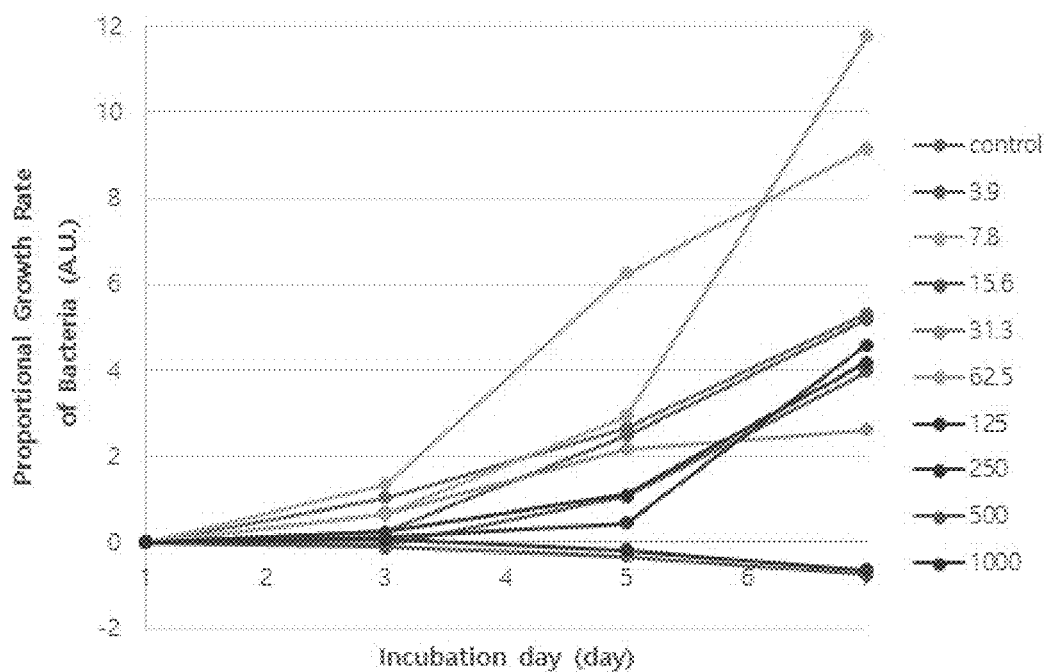

[Fig. 13]
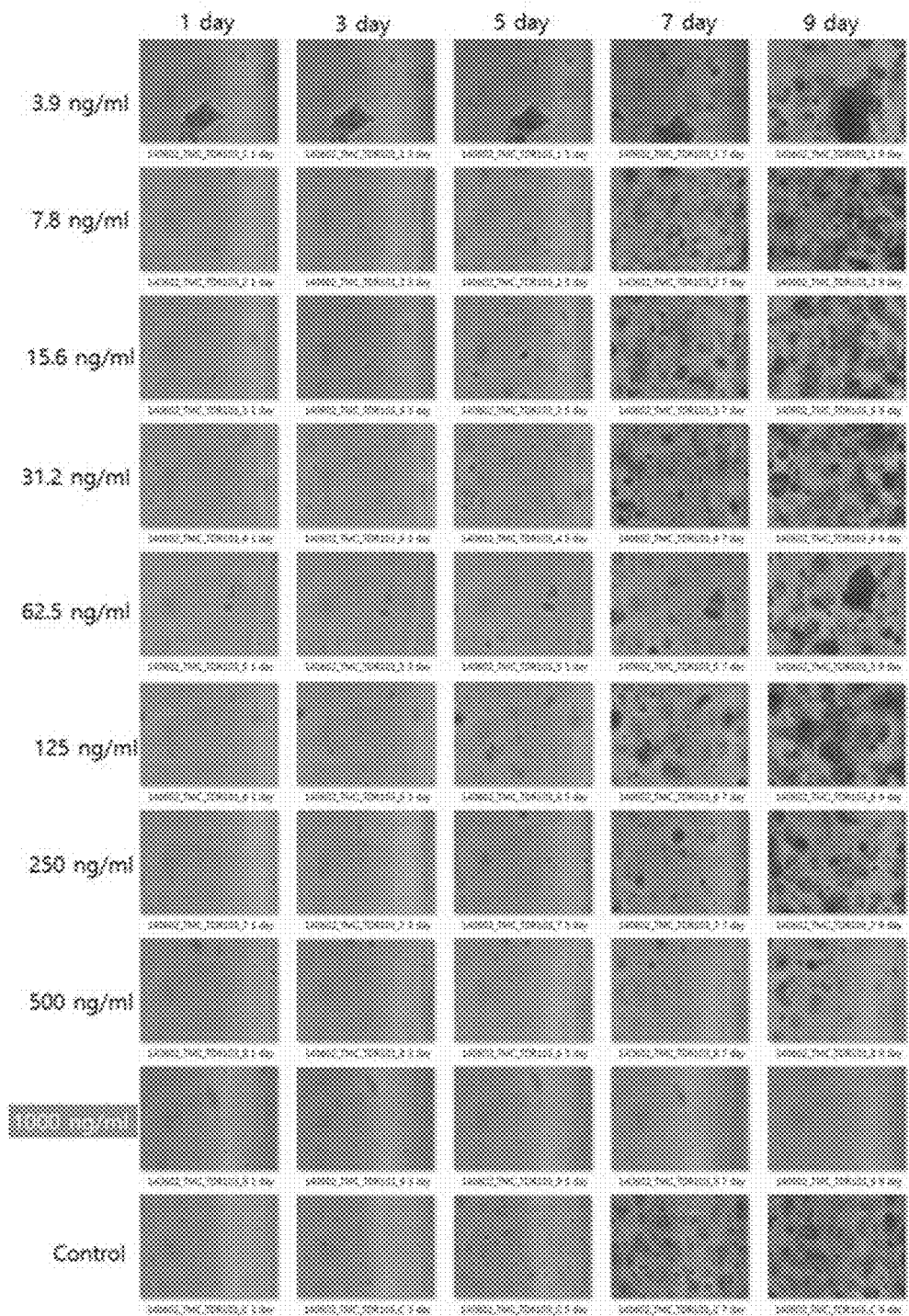

[Fig. 14]
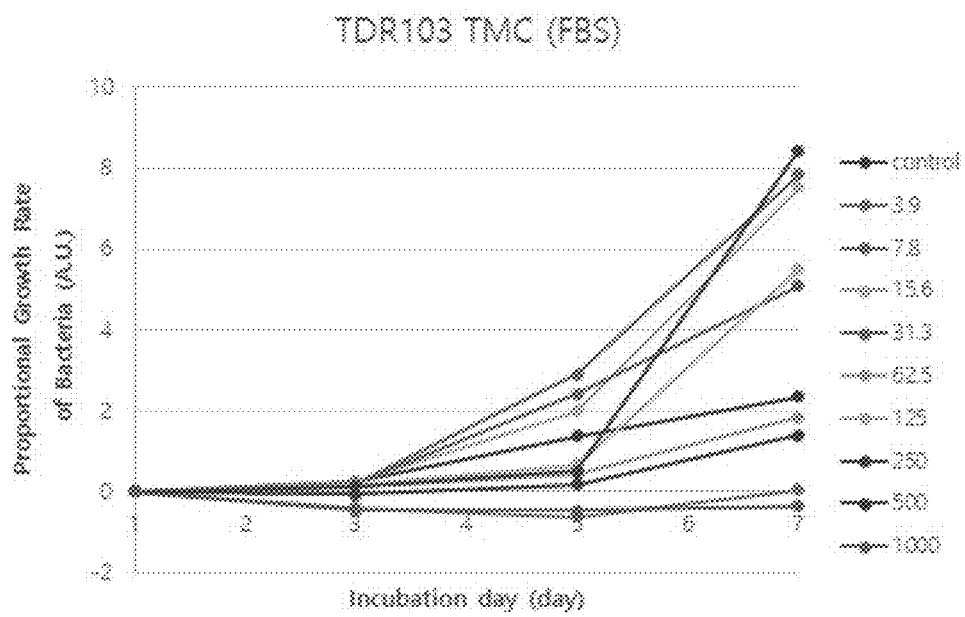
[Fig. 15]
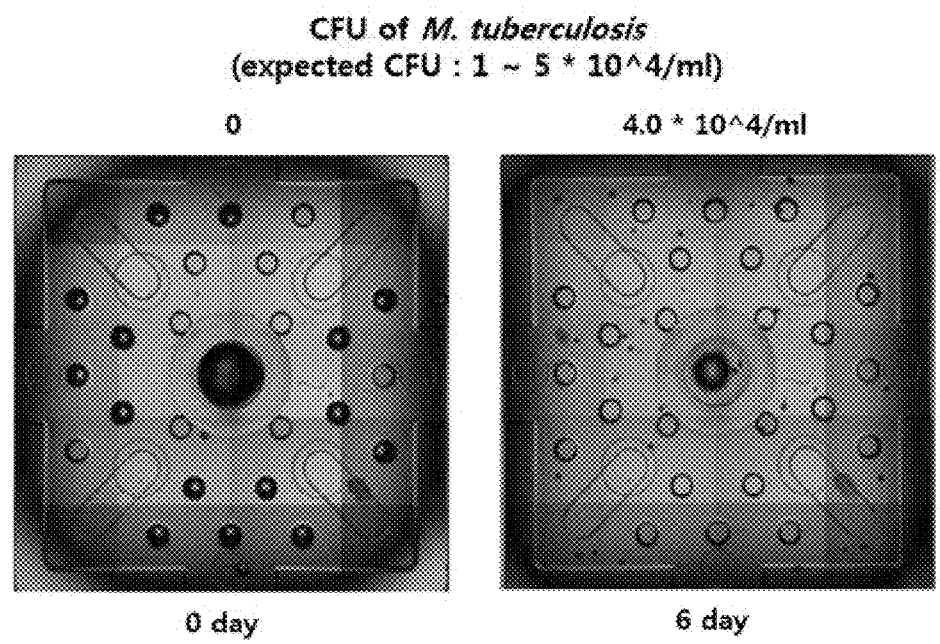

BIOACTIVITY TESTING STRUCTURE FOR SINGLE CELL TRACKING USING GELLING AGENTS

CROSS-REFERENCE TO RELATED APPLICATIONS

This application is the U.S. National Phase under 35 U.S.C. § 371 of International Application No. PCT/KR2014/009755 filed on Oct. 16, 2014, which in turn claims the benefit of Korean Application No. 10-2014-0139700, filed on Oct. 16, 2014, the disclosures of which are incorporated by reference into the present application.

TECHNICAL FIELD

The present invention relates to a novel bioactivity testing structure for single cell tracking using a gelling agent and a bioactivity testing system including the testing structure.

The present invention also relates to bioactivity testing, drug susceptibility testing, antibiotic screening, and diagnostic methods using the testing structure.

BACKGROUND ART

The infectious disease that threatens health of one third of the world's population is tuberculosis (TB). Despite the presence of anti-tuberculosis drugs, about 1% of the world's population contracts tuberculosis annually and 1.3 million people die from TB-Multidrug-resistant tuberculosis (MDR-TB) and extensively drug-resistant tuberculosis (XDR-TB) are gradually increasing due to poor managing the TB patients or TB suspicious groups. In recent years, the first case of totally drug resistant TB (TDR-TB) has been reported in India. To reduce transmission of TB and improve outcomes for TB patients, a rapid and accurate drug treatment after drug susceptibility test (DST) is necessary. Diagnosis of the resistance of TB to certain drugs among standard first-line anti-TB agents is very important in identifying MDR-TB, XDR-TB, and TDR-TB and preventing ineffective drug therapies.

General DST methods are based on culturing cells in solid and liquid media. According to solid medium culture methods, *Mycobacterium tuberculosis* (MTB) is inoculated into a solid medium supplemented with an antibiotic and the formation of colonies is observed by naked-eye detection. Since MTB grows slowly (the cells differentiate for about 24 hours), conventional DST methods take at least 4 to 6 weeks. The use of liquid media accelerates the growth of MTB to reduce the time required for DST. A commercial DST platform using liquid media called MGIT 960 system, is available. The MGIT system detects a fluorescence signals when MTB grows and consumes oxygen. The DST time of this MGIT system is as short as approximately 1 week. However, this method causes an increase in error rate because the growth of MTB cells is not directly observed but is indirectly identified.

A microscopic-observation drug susceptibility (MODS) method for direct observation was developed to reduce DST time. According to this method, a sputum sample together with a drug is inoculated into a 24-well plate and colony formation is monitored daily, which plays an important role in identifying whether MTB grows. This method can yield DST results within one week. However, single cells of MTB cannot be immobilized in liquid media, making it impossible to track the single cells. To obtain DST results, a microscopic observation over the entire well area is essential for the detection of colony formation and a long-term observation is inevitable.

Many lab-on-a-chip technologies have been developed for single cell tracking: an array of micro-scale wells, passive microfluidic trapping, an actively valved microfluidic system, and droplet microfluidics. In the array method using micro-scale wells and passive microfluidic trapping, the cells settle via gravity and are trapped in the weirs by fluid flow. However, the difficulty associated with controlling the fluidic environment hinders multiplex assays for drug testing. To better control cell and drug loading, actively valved microfluidics employs a computer-controlled, pneumatically actuated trapping method to precisely control small quantities of liquids via multiple control elements. However, this approach relies on complex control, which is associated with high costs and excessive operating efforts. Therefore, this method is not applicable for routine clinical drug testing. Droplet microfluidics employs a small number of chambers for multiplexing drug tests. However, these methods do not ensure the immobilization of bacterial cells in the liquid, which is necessary for single cell tracking.

Inoculum effect (IE) is an unwanted phenomenon in laboratory and may lead to overestimation of in vitro resistance, causing an increase in minimal inhibitory concentration (MIC). Consequently, inoculum effect deteriorates the reproducibility of experiments. Furthermore, since MIC is a parameter determining the microbiological efficacy of antibiotics in pharmacokinetics, different MIC values by cell densities may limit the clinical evaluation of antibiotics.

DETAILED DESCRIPTION OF THE INVENTION

Problems to be Solved by the Invention

The present inventors have earnestly and intensively conducted research to develop methods for effective and rapid diagnosis of bacteria, particularly, *Mycobacterium tuberculosis*, DST, and screening, and as a result, invented a new chamber (referred to as a "DAC system") to make a thin layer of an agarose mixture and have open surface on top of the thin layer for supplying liquid culture media and drugs. Further, the present inventors have found that the DAC system is effective for rapid and simple DST of drugs, drug screening, and tuberculosis diagnosis. The present invention has been achieved based on these findings.

Thus, one object of the present invention is to provide a novel bioactivity testing structure and a bioactivity testing system including the testing structure.

A further object of the present invention is to provide methods for bioactivity testing, antibiotic susceptibility testing of bacteria, antibiotic screening, and bacterial diagnosis using the bioactivity testing structure.

Means for Solving the Problems

One aspect of the present invention provides a bioactivity testing structure including a plate body, one or more culture units 100 arranged on the plate body, and a base plate 110 under which a solid thin film is to be formed on the bottom surface of each culture unit.

The bioactivity testing may be drug susceptibility, drug screening or bacterial culture diagnosis testing.

Each of the culture units may further have a receiving recess 120 formed on top of the base plate.

Each of the culture units may have an inlet 111 formed in the base plate and through which a mixture solution of a liquid medium containing a gelling agent and a biological agent is to be introduced.

Each of the culture units 100 may have one or more connection members 113 through which the base plate 110 is connected to barriers (partition walls) of the plate body and cut-away grooves 114 formed between the connection members.

Each of the culture units may have one or more through-holes 112 formed in the base plate 110.

Preferably, each of the culture units 100 has a size of 1-50 mm×1-50 mm and a height of 1 to 50 mm.

Preferably, the receiving recess 120 has a width of 1 to 5 mm and a height of 1 to 3 mm.

The mixture solution is solidified under the base plate to form a biological agent-immobilized solid thin film.

The thin film may have a thickness of 1 µm to 10 mm and the density of the biological agent in the mixture solution may be from $10^1$ to $10^{80}$ cfu/ml.

The gelling agent is not limited to a particular kind and may be agar, agarose, gelatin, alginate, collagen or fibrin.

A bioactive agent may be further introduced into the culture unit, and more preferably, the bioactive agent is introduced in a freeze-dried form into the receiving recess.

The plate body, the culture units, and the base plate may be made of a transparent or translucent material.

A further aspect of the present invention provides a bioactivity testing method including: providing a mixture solution of a liquid medium containing a gelling agent and a biological agent to the bottom surface of the bioactivity testing structure; solidifying the mixture solution to form a solid thin film in which the biological agent is immobilized; supplying a bioactive agent to the solid thin film and allowing the bioactive agent to diffuse into the solid thin film; and observing the individual responses of the single cells of the biological agent to the bioactive agent or observing whether the biological agent forms colonies or the colony forming units (CFU).

The method may further include imaging the individual responses of the single cells of the biological agent to the bioactive agent, the colonies of the biological agent or the colony forming units (CFU), and analyzing the images. More preferably, the method further includes determining the minimum inhibitory concentration (MIC) of the bioactive agent based on the analysis of the images.

The present invention also provides a method for antibiotic susceptibility testing of bacteria, including: providing a mixture solution of a liquid medium containing a gelling agent and a bacterial strain to the bottom surface of the bioactivity testing structure; solidifying the mixture solution to form a solid thin film in which the bacterial strain is immobilized; supplying an antibiotic to the solid thin film and allowing the antibiotic to diffuse into the solid thin film; and observing the individual responses of the single cells of the bacterial strain to the antibiotic or observing whether the bacterial strain forms colonies or the colony forming units (CFU).

Preferably, the method further includes imaging the individual responses of the single cells, the colonies or the colony forming units (CFU), analyzing the images, and determining the minimum inhibitory concentration (MIC) of the antibiotic based on the analysis of the images.

The bacterial strain may be *Mycobacterium tuberculosis* or a nontuberculous mycobacterium (NTM). The *Mycobacterium tuberculosis* may be multi-drug-resistant (MDR) tuberculosis, extensively drug-resistant (XDR) tuberculosis or totally drug-resistant (TDR) tuberculosis.

The method shows no inoculum effect.

Another aspect of the present invention provides an antibiotic screening method including: providing a mixture solution of a liquid medium containing a gelling agent and a bacterial strain to the bottom surface of the bioactivity testing structure; solidifying the mixture solution to form a solid thin film in which the bacterial strain is immobilized; supplying an antibiotic to the solid thin film and allowing the antibiotic to diffuse into the solid thin film; and observing the individual responses of the single cells of the bacterial strain to the antibiotic or observing whether the bacterial strain forms colonies or the colony forming units (CFU).

The method may further include imaging the individual responses of the single cells, the colonies or the colony forming units (CFU), analyzing the images, and determining the minimum inhibitory concentration (MIC) of the antibiotic based on the analysis of the images.

Another aspect of the present invention provides a bacterial diagnostic method including: providing a mixture solution of a liquid medium containing a gelling agent and a bacterial strain to the bottom surface of the bioactivity testing structure; solidifying the mixture solution to form a solid thin film in which the bacterial strain is immobilized; supplying a culture medium of the bacterial strain to the solid thin film and allowing the culture medium to diffuse into the solid thin film; and observing the individual responses of the single cells of the bacterial strain or observing whether the bacterial strain forms colonies or the colony forming units (CFU).

The culture medium of the bacterial strain may be further supplemented with an antibiotic and the diagnostic method may be carried out simultaneously with drug susceptibility testing.

Yet another aspect of the present invention provides a bioactivity testing system including: the bioactivity testing structure including culture units in which a bioactive agent is provided and a base plate under which a mixture solution of a liquid medium containing a gelling agent and a biological agent is solidified to form a thin film on the bottom surface of each culture unit; a stage for supporting and observing the testing structure; and a measurement system for imaging the individual responses of the single cells of the biological agent or the formation of colonies of the biological agent when the bioactive agent is delivered by diffusion or imaging the colony forming units (CFU), analyzing the images, and determining the minimum inhibitory concentration (MIC) of the bioactive agent based on the analysis of the images.

The measurement system may include an imaging system and an image processing system.

Effects of the Invention

The bioactivity testing structure of the present invention enables very rapid and simple drug susceptibility testing of bacteria, particularly *Mycobacterium tuberculosis*, drug screening, and bacterial diagnosis. Particularly, the use of the testing structure enables DST and diagnosis of bacteria only by pretreatment without the need to concentrate human sputum samples irrespective of inoculum effect, ensuring rapid, accurate, and simple testing compared to conventional tuberculosis diagnosis or DST systems. In addition, the testing structure of the present invention simultaneously enables the diagnosis and drug susceptibility testing of tuberculosis. Therefore, the present invention provides an effective alternative to the prior art.

BRIEF DESCRIPTION OF THE DRAWINGS

FIG. 1 shows a schematic diagram of a DAC chip according to the present invention.

FIGS. 2a and 2b are perspective and plan views of a first embodiment of a testing structure according to the present invention, respectively.

FIGS. 3a and 3b are plan and perspective views of a second embodiment of a testing structure according to the present invention, respectively.

FIG. 4 shows a detailed diagram of a DAC chip and a DST method using the DAC chip.

FIG. 5 shows diffusion of rhodamine B as an antibiotic from agarose.

FIG. 6 shows time lapse images and processed images of *M. tuberculosis* upon drug susceptibility testing.

FIG. 7 shows growth curves of resistant and susceptible cases plotted by processing the images of FIG. 6 using sequential digital data.

FIG. 8 compares the times required for the detection of *M. tuberculosis* growth in 49 H37Rv sputum samples by the N-acetyl-L-cysteine-NaOH (NALC-NaOH) method on DAC and MGIT 960 systems.

FIG. 9 compares the results of the NALC-NaOH method or direct inoculation method (without concentration) on DAC and MGIT 960 systems.

FIG. 10 shows the numbers of colonies counted in 7H11 media for the calculation of inoculum concentrations.

FIG. 11 shows images showing the growth of a first clinical strain isolated from a TDR 102 patient at various concentrations of a drug to calculate the MIC of the drug.

FIG. 12 is a graph obtained by quantifying the images of FIG. 11.

FIG. 13 shows images showing the growth of a second clinical strain isolated from a TDR 103 patient at various concentrations of a drug to calculate the MIC of the drug.

FIG. 14 is a graph obtained by quantifying the images of FIG. 13.

FIG. 15 shows microscopic time-lapse images together with a time-lapse colony forming units (CFU) of *M. tuberculosis* (MTB).

BEST MODE FOR CARRYING OUT THE INVENTION

The present invention will be explained in more detail with reference to the following examples. However, these examples are provided for illustrative purposes only and are not intended to limit the scope of the invention.

Example 1: Development of DAC System and Verification of DST 1.1. Sample

Agarose was used as a MTB fixing material. The agarose solution was mixed with a stock solution of TB, which posed a risk of thermal shock if a high-temperature agarose solution was used. To reduce this risk, an agarose concentration of 0.5% was used because this concentration is sufficiently low to prevent solidification at 37° C. Lower concentrations of agarose enhance the diffusion of the culture medium and drug. The drugs used for the DST were purchased from Sigma-Aldrich. The liquid culture medium was Middlebrook 7H9 broth supplemented with 10% OADC.

1.2. Strains

The standard strains, *M. tuberculosis* H37Rv, and clinical strains, MDR and XDR-TB, were obtained from the Korean Institute of Tuberculosis. The TB strains were pre-cultured on LJ medium until there were several colonies for a DST process.

1.3. Design and Fabrication of Chip

For the microscopic tune-lapse imaging of TB, a test chip was necessary to immobilize the TB in agarose to ensure the sufficient delivery of drugs and optical transparency. To satisfy these requirements, a new chip, the Disc Agarose Channel (DAC) chip, was designed and fabricated.

A schematic diagram of the DAC chip is shown in FIG. 1.

Detailed perspective and plan views of the DAC chip are illustrated in FIGS. 2a and 2b and FIGS. 3a and 3b.

The DAC chip consists of a disc-shaped channel (base plate), which was loaded with the agarose and TB mixture. The chip also features structures to enhance the diffusion of the culture medium and drugs, such as wells that contain culture medium, drug, open spaces, and holes.

Specifically, the DAC chip consists essentially of one or more culture units arranged on a plate body and a base plate under which a solid thin film is to be formed on the bottom surface of each culture unit. Each of the culture units may further have a receiving recess formed on top of the disc-shaped channel (base plate). Each of the culture units may have an inlet formed in the base plate and through which agarose and TB mixture is to be introduced. Each of the culture units has one or more connection members through which the base plate is connected to barriers of the plate body and cut-away grooves formed between the connection members. Each of the culture units may have one or more through-holes formed in the base plate. The depth of the disc-shaped channel (ex. 300 µm) is determined by the height of a spacer. The DST of TB requires a long incubation time and a sufficient amount of culture medium should be supplied to TB. However, the use of a syringe pump to supply medium is inconvenient and limits the throughput of the system. Therefore, each well was designed to have the same size as that of a single well in a 24-well plate. Specifically, the diameter of the well is 11 mm, and the height of the well is 10 mm. The wells contained 1 ml of medium, which is suitable for more than 1 month of incubation.

The fabrication of chips using PDMS limits the dimensions of the chip, and the manufacturing throughput is low. Therefore, injection molding was used to fabricate the DAC chip. After designing the chip using a 3D design tool (SolidWorks), the aluminum mold was machined. Poly (methyl methacrylate) (PMMA) was used to generate the chips. After the fabrication of chips, a polycarbonate film was bonded to the bottom of the chip using the solvent-bonding method. Chamber was manufactured by 3D design tool and injection molding process. Also, lower film, the polycarbonate was bonded under pressure (80% of ethanol and 20% of 1,2-dichloroethane in weight, Sigma-Aldrich). The chip was then subjected to $O_2$ plasma treatment to ensure hydrophilicity. The chip was then treated with gamma rays for 5 h for sterilization.

1.4. DST Process

For DST in the DAC chip, the chip was subjected to $O_2$ plasma treatment to ensure hydrophilicity and was then treated with gamma radiation for sterilization. TB stock solutions were prepared by collecting colonies from LJ medium using a sterilized loop. The aggregated colonies were dispersed in a U-shaped bottom tube by vortexing with 2-mm diameter glass beads. Due to safety concerns, the vortexed tube was allowed to rest for 15 min. After stabilization, 7H9 medium containing 10% OADC was added to prepare the stock solution containing McFarland 1.5-3.0. The stock solution was mixed with 0.5% agarose at 37° C. by vortexing. Subsequently, 40 μl of 0.375% agarose mixture with TB stock was loaded into the inlet of DAC chip. The agarose was then allowed to solidify at room temperature for 1 min. A 0.5-ml aliquot of 7H9 containing 10% OADC and TB drugs was then added to the DAC chip. The drug in the culture medium was then allowed to diffuse into the agarose. After this process, the DAC chip was then sealed by an air-permeable film to prevent the evaporation of the culture medium and incubated in a temperature-controlled culture chamber at 37° C. One area at the edge of the agarose was imaged with a ×40 lens on an inverted microscope every day using the time-lapse method. These procedures were all carried out on a clean bench.

1.5. Use of 3D Culture DAC Chip for the DST of MTB

In the present invention, agarose was used as a 3D culture matrix for the DST of MTB. A stable 3D culture matrix was necessary for the long-term incubation of MTB.

FIG. 4 shows a detailed diagram of a DAC chip and a DST method using the DAC chip. To verify the stability of the agarose matrix, 0.5% agarose was mixed with microbeads at a ratio of 3:1 by volume in phosphate buffered saline. The mixture was loaded into the inlet of the DAC chip and 7H9 culture medium was added to the wells. For the DST conditions of MTB, the chip was cultured in the chamber at 37° C. The beads in the agarose matrix were well observed at the same areas for 3 weeks, indicating that the 3D culture matrix is sufficiently stable for the DST of MTB. When H37Rv was cultured in the agarose matrix, the structure was also well maintained during single cells tracking for 3 weeks. To ensure a uniform supply of liquid culture medium and drug, the agarose matrix was properly formed in the mold. To visualize the formation of the agarose matrix, a 0.5% agarose mixture containing food dye at a ratio of 3 (food dye):1 (agarose) by volume was loaded into the chip and imaged. The agarose matrix was well formed on the DAC chip.

1.6. Diffusion Characteristics in the DAC Chip

Agarose was used to immobilize TB. The TB drugs were dissolved in a liquid medium, 7H9 broth, to be delivered to the agarose matrix. In the present invention, the concentration of drugs at the corner of the DAC chip (the imaging area) needed to be uniform to ensure accurate DST results. The time required for a small molecule (molecular weight 200) to diffuse to the imaging area was calculated. The concentrations of the molecule in the imaging areas were the same. Rhodamine B (molecular weight, 479.02 g/mol) was used to visualize the diffusion characteristics of the agarose matrix in the DAC chip because its molecular weight is similar to that of the TB drugs. The chips were treated with various concentrations of these molecules and imaged at 0, 10, 30, and 60 min to assess the uniformity of diffusion. The fluorescent signal became uniform within 30 min of loading the fluorescent dye, implying that this system is suitable for a DST (considering the cell division of MTB, which is approximately 20-24 h). The growth rate of MTB was the same over the entire region of the chip, which demonstrates the diffusion of the liquid culture medium and drug at the same level in the chip.

FIG. 5 shows diffusion of the antibiotic rhodamine B from the agarose. Specifically, in FIG. 5, A shows an image taken immediately after rhodamine B was loaded, and B, C, and D show images taken at intervals of 10 min in sequence. The diffusion time was 0.1 sec.

1.7. Tracking of Single Cells in the DAC Chip

Conventional DST methods rely on the measurement of MTB growth via the macroscopic observation of colony formation on a solid medium or on indirect fluorescence-based detection methods that measure oxygen consumption in liquid medium.

The single cell growth tracking method of the present invention was used for measurement of the MTB growth under various drug conditions. The MTB cells on the DAC chip were tracked every day for several days. One imaging area (200 μm×300 μm) contained many different sizes of TB because the MTB cells were prepared from colonies (the big cluster form) on solid medium.

1.8. Image Processing for Automatic Susceptibility Determination

The conventional DST method on solid medium (LJ medium) relies on the macroscopic assessment of MTB growth by an experienced experimenter. Thus, this method is subject to human error.

In the present invention, automatic image processing was employed to determine the drug susceptibility of MTB and avoid human error. The microscopic time lapse images with CCD camera were processed to digitalize the MTB growth under TB drug conditions. The raw images from CCD camera were processed to a binary format. Although not all white areas represent growing MTB cells because the boundaries of MTB colonies were not clear and the imaging area contained some debris, white most areas were due to the growth of MTB in the agarose matrix and consequently proportional to this parameter.

FIG. 6 shows the time lapse images and processed images.

A) and A') are resistant cases and B) and B') are susceptible cases. In the resistant cases, the formation of many colonies in the imaging area was found. After image processing, the white areas represent growing MTB colonies in the image. In the susceptible cases, there were no differences in MTB growth in the images.

The white area in the images was calculated by counting the pixel number. Using sequential digital data, the growth curve according to the time was plotted in FIG. 7. By setting the threshold value, drug susceptibility of TB strains under various concentrations of TB drugs was determined.

FIG. 7 shows quantified growth curves of the resistant and susceptible cases. The growth curves were constructed by measuring the growth areas of MTB in the images. Bacterial areas were continuously increased in the resistant case whereas no substantial changes were observed in the susceptible case.

1.9. DST of MTB Using the DAC System

MTB DSTs are based on the estimation or measurement of the growth or non-growth of a MTB strain in the presence of a single "critical concentration" of one drug. The critical concentration of an anti-TB drug indicates clinically relevant resistance if growth is observed, whereas susceptible MTB strains are inhibited at the critical concentration. In the DAC system, the critical concentration of each anti-TB drug is determined by the critical concentration of the MGIT because the DAC system is more similar to the liquid culture system than the solid culture system. After determining the critical concentration of each anti-TB drug, DSTs were conducted using the DAC system at serial twofold concentrations near the critical concentration to acquire the minimum inhibitory concentration (MIC) and susceptibility of MTB.

The MIC values of anti-TB drugs could be determined through sufficient tests at concentrations of the drugs. Thereafter, when the MIC value was at or below the critical concentration, the strain was considered to be susceptible, whereas resistant strains were defined by MIC values that exceed the critical concentration. Specifically, the critical concentration of rifampin is 1.0 μg/ml in the DAC system. The DST using the DAC system was performed at 0.25, 0.5, 1.0, and 2.0 μg/ml concentrations of rifampin. Growth curves were plotted from the concentration of each anti-TB drug according to the incubation time. Susceptibility was determined by measuring MIC value based on the critical concentration.

As the number of patients infected with MDR, XDR, and TDR increases throughout the world, rapid DST is urgently needed for public health and diagnosis. The DAC system enables rapid DST based on the concept of microfluidic channels. To validate the DAC system for rapid SDT, virulent standard strain of MTB, H37Rv and clinical strains of MDR and XDR strains were tested to determine the susceptibility of isoniazid, rifampicin, streptomycin, and ethambutol.

The conventional U medium-based DST was used for quality control and as a comparison target because it is regarded as the 'gold standard' of DST. The MIC values of isoniazid, rifampicin, streptomycin, and ethambutol against H37Rv, MDR, and XDR were determined by using the DAC system.

From these MIC values, the susceptibility of H37Rv, MDR, and XDR to isoniazid, rifampicin, streptomycin, and ethambutol was determined below the critical concentrations or by measuring MIC values at concentrations other than the critical concentration.

The images of all tested strains were taken at the same position every other day for 5 days using the time-lapse method. The images were processed using the daily time-lapse data for 5 days and were plotted to determine the MIC values of the four anti-TB drugs.

The results are shown in Table 1.

TABLE 1

| DST results measured using the DAC system ||||
| Sample# | H37Rv | MDR | XDR |
| --- | --- | --- | --- |
| A ||||
| INH | 0.05 | >0.2 | >0.2 |
| RFP | 0.25 | >2.0 | >2.0 |
| SM | 2.0 | >4.0 | >4.0 |
| EMB | 5.0 | >10.0 | 10.0 |

TABLE 1-continued

| DST results measured using the DAC system ||||
| Sample# | H37Rv | MDR | XDR |
| --- | --- | --- | --- |
| B ||||
| INH | S | R | R |
| RFP | S | R | R |
| SM | R | R | R |
| EMB | S | R | R |

The susceptibility of H37Rv, MDR, and XDR TB strains to four primary TB drugs, isoniazid (INH), rifampicin (RFP), streptomycin (SM), and ethambutol (EMB) was tested. The test concentrations were determined from the critical concentrations of the respective drugs.

After MIC determination in the time-lapse images, the values were tested by brake points and drug susceptibility was determined.

In Table 1, A shows MIC values of DST obtained from the DAC system and B shows susceptibility determined from the MIC data and the critical concentrations of the drugs.

As can be seen from A in Table 1, isoniazid, rifampicin, streptomycin, and ethambutol had MIC values of 0.05 μg/ml, 0.25 μg/ml, 2.0 μg/ml, and 5.0 μg/ml, respectively. From the MIC data, the strain H37Rv was found to be sensitive to isoniazid, rifampicin, streptomycin, and ethambutol. The same results were obtained also in LI culture tests.

The other two test strains from MDR and XDR patients were found to be resistant to all drugs in the DAC system. The sensitivity results were demonstrated using the LJ culture method regarded as the gold standard. All susceptibility results in the DAC system were consistent with the results from the gold standard method. From these verified results, it was demonstrated that the DAC system can reduce DST time and be used for accurate diagnosis of susceptibility and resistance to the anti-tuberculosis drugs.

Example 2: Comparison of the DAC System with Conventional Culture Diagnostic Products The usefulness of the DAC system was confirmed by comparing the DAC system of the present invention with conventional TM culture diagnostic methods.

2.1. Comparison of Recovery Rates

Three divided portions of the same sputum sample were tested in three systems. The results were compared.

Specifically, tests were conducted on 6/25 smear-positive pulmonary tuberculosis patients. In the 25 clinical sputum samples, 3 positive samples were found (positive rate 12.0%). In the three positive samples, one was positive in Ogawa's medium, Middlebrook 7H11 medium, and the DAC system, another was positive in 7H11 medium and the DAC system, and the other was positive in the DAC system. The numbers of negative samples in Ogawa's medium, Middlebrook 7H11 medium, and the DAC system were 23 (negative rate 92.0%), 22 (negative rate 88.0%), and 21 (negative rate 84.0%), respectively. In all methods, one sample was contaminated (4.0%).

The recovery rates of *M. tuberculosis* in the three culture methods were compared. As a result, a higher recovery rate (12.0%) was obtained in the DAC system than in Ogawa's medium (4.0%) and Middlebrook 7H11 medium (8.0%). Contamination rates in the three methods were the same.

Detailed comparison results are shown in Table 2.

ture diagnostic time of the DAC system according to the present invention was compared with that of the prior art.

The results are shown in FIG. 8.

FIG. 8 compares the times required for the detection of *M. tuberculosis* growth in 49 H37Rv sputum samples by the

TABLE 2

| | | No.(%) of specimens with result determined by: | | | | | | | | |
|---|---|---|---|---|---|---|---|---|---|---|
| | Total no. of | Ogawa's medium (n = 25) | | | Middlebrook 7H11 medium (n = 25) | | | DAC sysem (n = 25) | | |
| Smear grade | Specimens (n = 25) | Positive samples | Negative samples | Contamination | Positive samples | Negative samples | Contamination | positive samples | negative samples | Contamination |
| Negative Scanty | 19 (76.0) | | 19 (76.0) | | | 19 (76.0) | | | 19 (76.0) | |
| 1+ | 3 (12.0) | | 2 (8.0) | 1 (4.0) | | 2 (8.0) | 1 (4.0) | | 2 (8.0) | 1 (4.0) |
| 2+ | 2 (8.0) | | 2 (8.0) | | 1 (4.0) | 1 (4.0) | | 2 (8.0) | | |
| 3+ | 1 (4.0) | 1 (4.0) | | | 1 (4.0) | | | 1 (4.0) | | |
| Total | 25 (100.0) | 1 (4.0) | 23 (92.0) | 1 (4.0) | 2 (8.0) | 22 (88.0) | 1 (4.0) | 3 (12.0) | 21 (84.0) | 1 (4.0) |

2.2. Comparison of Colony Forming Units (CFU) with the Prior Art

After pretreatment of 49 H37Rv sputum samples, the samples were inoculated in the DAC system and Middlebrook 7H11 medium and their colony forming units (CFU) were counted. The initial CFU was $1 \times 10^4$/ml. The CFU values in the sputum samples were counted by the culture method. As a result, the CFU value in the DAC system was found to be similar to that obtained in Middlebrook 7H11 medium by a conventional method. However, the CFU result was obtained in the DAC system in 9 days and was obtained in Middlebrook 7H11 medium in about 21 days. The median CFU in the DAC system was 4.27 $\log_{10}$ CFU/ml (SD±0.75) and that in Middlebrook 7H11 medium was 4.32 $\log_{10}$ CFU/ml (SD±0.64). (FIG. 15)

2.3. Comparison of Culture Detection Times with the Prior Art

The tuberculosis culture diagnosis or the U medium method used in the DST system takes 4 to 6 weeks. MGIT 960 (BD BACTEC™) is currently the fastest product for culture diagnosis of *Mycobacterium tuberculosis*. The cul- N-acetyl-L-cysteine-NaOH (NALC-NaOH) method on DAC and MGIT 960 systems.

As shown in FIG. 8, TTD was 5-13 days in the MGIT 960 system and 5-9 days in the DAC system. The highest detection level of *M. tuberculosis* was 7 days in the MGIT 960 and DAC systems.

TTD values at different inoculum concentrations of *M. tuberculosis* were compared and the results are shown in Table 3.

TABLE 3

| Sample (n = 49) | Predictor | No.(%) of positive samples | Median TTD (day) | | | | | | | | |
|---|---|---|---|---|---|---|---|---|---|---|---|
| | | | 5 | 6 | 7 | 8 | 9 | 10 | 11 | 12 | 13 |
| MGIT 960 system | No. of H37Rv ($\log_{10}$ cfu/ml) | | | | | | | | | | |
| | Contamination | 4 (8.2) | | | | | | | | | |
| | 2-3 | 2 (4.1) | | | | | | | | 1 | 1 |
| | 3-4 | 7 (14.3) | 1 | 1 | 5 | | | | | | |
| | 4-5 | 28 (57.1) | | 1 | 22 | 5 | | | | | |
| | 5-6 | 8 (16.3) | 7 | 1 | | | | | | | |
| | Total | 49 (100.0) | | | | | | | | | |
| DAC system | Contamination | | | | | | | | | | |
| | 2-3 | 2 (4.1) | | | | | | 2 | | | |
| | 3-4 | 10 (20.4) | | 2 | 6 | | | 2 | | | |
| | 4-5 | 28 (57.1) | 5 | 10 | 10 | 3 | | | | | |
| | 5-6 | 9 (18.4) | | | 9 | | | | | | |
| | Total | 49 (100.0) | | | | | | | | | |

Specifically, a total of 49 H37Rv sputum samples were used to detect *M. tuberculosis* in order to determine TTD values according to CFU values in Middlebrook 7H11 media.

In the DAC system, the times required for the detection of *Mycobacterium tuberculosis* were 1, 5, 6, 7, 8, 9, 10, 11, 12, 13, 14, 21, 28, 35, and 42 days.

The median TTD values according to CFU values in Middlebrook 7H11 media were from 7 days (5-6 $\log_{10}$ CFU/ml) to 9 days (2-3 $\log_{10}$ CFU/ml) in the DAC system.

The TTD values according to CFU values in the Middlebrook 7H11 media were from 6 days (5-6 $\log_{10}$ CFU/ml) to 12 days (2-3 $\log_{10}$) CFU/ml) in MGIT 960 system.

When the count of *M. tuberculosis* was 2-3 $\log_{10}$ CFU/ml, the median TTD values of *M. tuberculosis* in the MGIT 960 and DAC systems were 12 days and 9 days, respectively.

When the count of *M. tuberculosis* was 3-4 $log_{10}$ CFU/ml, the median TTD values of *M. tuberculosis* in the MGIT 960 and DAC systems were 8 days and 7 days, respectively.

When the count of *M. tuberculosis* was 4-5 $log_{10}$ CFU/ml, the median TTD values of *M. tuberculosis* in the MGIT 960 and DAC systems were 7 days and 6 days, respectively.

When the count of *M. tuberculosis* was 5-6 $log_{10}$ CFU/ml, the median TTD values of *M. tuberculosis* in the MGIT 960 and DAC systems were 6 days and 7 days, respectively.

When the count of *M. tuberculosis* was 2-5 $log_{10}$ CFU/ml, the detection of *M. tuberculosis* growth was rapid in the DAC system (ranging from 6 to 9 days) compared to in the MGIT 960 system (ranging from 7 to 12 days). When the count of *M. tuberculosis* was 5-6 $log_{10}$ CFU/ml, the detection of *M. tuberculosis* growth was rapid in the MGIT 960 system (6 days) compared to in the DAC system (7 days).

The median TTD was 7 days in the DAC1 (5-7 days), DAC2 (5-7 days), and MGIT1 systems (6-7 days).

In contrast, in the MGIT2 system, the median TTD required for the detection of *M. tuberculosis* from the samples was 14 days (7-24 days).

No contamination was observed in the DAC system whereas 5.6% and 27.8% were contaminated in the MGIT1 and MGIT2 systems, respectively.

That is, positive samples were found between 5-7 days in the DAC culture method irrespective of sputum pretreatment. In contrast, positive samples were found between 6-7 days and a low false positive rate was obtained in the MGIT 960 culture method when the sputum samples were pretreated according to the NALC-NaOH method recommended by the supplier.

2.5. Comparison of the Times Required to Obtain True Negative Results

For the liquid medium-based MGIT 960 system, 6 weeks were required for the detection of mycobacteria.

The times required to obtain true negative results using the DAC system were measured. The results are shown in Table 4.

TABLE 4

Times required for the detection of *Mycobacterium tuberculosis* growth

| Positive sample | TTD (day) | | | | | | | | | |
|---|---|---|---|---|---|---|---|---|---|---|
| (n = 52) | 5 | 6 | 7 | 8 | 9 | 10 | 11 | 12 | 13 | 14 |
| Recovery rates of *M. tuberculosis* (%) | 11.5 | 34.6 | 82.7 | 82.7 | 96.2 | 96.2 | 96.2 | 96.2 | 96.2 | 100.0 |

4 (8.2%) of the 49 samples were contaminated in the MGIT 960 system. *M. tuberculosis* in liquid cultures showed to be higher false positive rates than in the DAC system.

2.4. Comparison of the MGIT960 and DAC Systems Using the Direct Inoculation Method After sputa were decontaminated, the efficiencies of the MGIT960 and DAC systems were compared using the direct inoculation method (without concentration).

The results are shown in FIG. 9.

FIG. 9 compares the results of the NALC-NaOH method (with concentration) or the direct inoculation method (without concentration) on the MGIT 960 and DAC systems.

1, 5, 6, 7, 8, 9, 10, 11, 12, 13, 14, 21, 28, 35, and 42 days were required for the detection of *M. tuberculosis* growth using the DAC system.

Prior to inoculation, 18 H37Rv sputum samples were decontaminated with 2% NALC-NaOH and were divided into 2 specimens. One specimen was centrifuged at 3,000 g for 15 min in accordance with the standard NALC-NaOH method and the other specimen was used in the direct method (without concentration). The samples pretreated with the NALC-NaOH method (with concentration) and the direct method (without concentration) were cultured in the MGIT 960 and DAC system, respectively.

The above two sputum pretreatment method such as the DAC system culture method using the direct pretreatment method (without concentration) and the MGIT 960 culture method using the NALC-NaOH method (with concentration) method were found to have similar culture patterns.

The times required for the detection of *M. tuberculosis* growth in three clinical sputum samples (3 positive samples of the 25 clinical sputum samples) and 49 H37Rv sputum samples depending on the recovery rate of mycobacteria in the DAC system are shown in the above Table 4. The times required for the detection of *M. tuberculosis* in the DAC system were 1, 5, 6, 7, 8, 9, 10, 11, 12, 13, 14, 21, 28, 35, and 42 days.

In a total of 74 samples, 52 samples were positive, 22 samples were negative, and none of the samples were contaminated. 6 (11.5%) of the 52 positive samples were changed from negative to positive when determined at day 5, 50 (96.2%) of the 52 positive samples were changed from negative to positive when determined at day 9, and all samples were changed from negative to positive when determined at day 14. None of the 22 negative samples were changed up to 42 days. From these results, it is determined that significant culture results are obtained at day 9 in the DAC system ($p<0.05$) and all accurate culture results are obtained at day 14. It appears that the DAC system can-rapidly determine true negative results by about 28 days than the MGIT 960 system.

Example 3: Identification of the Presence of Inoculum Effect (IE) in the DAC System The present inventors evaluated the antibacterial activities of rifampin, isoniazid, ethambutol, and streptomycin as primary drugs against TB using the DAC system and whether the DAC system was affected by changes in cell density. This system can draw reproducible and reliable MIC values of the drugs irrespective of inoculum size.

3.1. Samples and Growth Conditions

*M. tuberculosis* was isolated from a pulmonary tuberculosis patient in the Korean Institute of Tuberculosis (KIT). For a total of 150 clinical strains including 134 pan-susceptible strains and 59 resistant strains, were identified for drug susceptibility using the L-J method before use. All isolates were freshly pre-cultured on L-J medium before use.

Sputum samples were digested and decontaminated by the N-acetyl-L-cysteine-NaOH method described by Kent and Kubica. The treated samples were cultured in MGIT vials for 42 days. On the day of detection, the presence or absence of AFB in all positive tubes was examined by ZN staining and drug susceptibility testing was conducted with parallel tubes.

Three clinical ESBL *E. coli* strains and one non-ESBL *E. coli* ATCC strain were used for lactamase substrate analysis. The *E. coli* strains were grown, subcultured, and analyzed on Mueller-Hinton agar (Difco) in Mueller-Hinton broth (Difco Laboratories, Detroit, Mich.).

3.2. Antibiotics

All drugs were purchased from Sigma-Aldrich (St. Louis, Mo.). As recommended by the supplier, powders were stored in a desiccator before use. Isoniazid (INH), ethambutol (EMB), streptomycin (SM), and cefepime were dissolved in deionized water (DW), and rifampicin (RIF) was dissolved in DMSO. All stock solutions were sterilized by membrane filtration through 0.22 µm pore Millex-GS filter units (Millipore, Bedford, Mass.). Small aliquots of each stock antibiotic solution were stored at −80° C. The freeze-dried drug solutions were used immediately after thawing and the remainder was discarded without the need to store in a freezer. Working solutions were freshly prepared from the stock solutions and were sequentially diluted to achieve desired concentrations.

3.3. DST Using the DAC System

*Mycobacterium tuberculosis* identified by ZN staining and grown from an L-J slope or MGIT tube and was subjected to DST. For the preparation of inoculation from the LJ culture, colonies up to 14 days were extracted from the grown culture. The colonies were shaken with glass beads to crush large lumps. To obtain a high density ($\sim 5 \times 10^9$ CFU/ml), the suspension was centrifuged at 3000 g for 10 min and pellets were resuspended in sterile PBS. Subsequently, the suspension was added to liquid agarose, inoculated in a bacteria-agarose mixture within the range of $10^1$ to $5 \times 10^8$ CFU/ml, and loaded in the main channel After solidification, 7H9 broth containing each antibiotic was applied to the chamber. All bacterial cells were imaged with an inverted optical microscope (IS71, Olympus).

3.4. L-J Proportion Method and DST Using the MGIT 960 System

The LJ proportion method was used as a reference. All strains were tested according to the standard procedures on L-J media at concentrations of 40 µg/ml (RIF), 0.1 µg/ml (INH), 2.0 µg/ml (EMB), and 1.0 µg/ml (SM), except that they were inoculated in the range of $10^1$ to $5 \times 10^8$ CFU/ml.

Also in DST using the MGIT 960 system, all strains were tested according to the supplier recommendation except for the inoculum size.

For the preparation of inoculum on the day of detection, all positive tubes were examined for the presence or absence of AFB by ZN staining. 0, 3, 10, and 15 days after the positive reaction, drug susceptibility testing was conducted with parallel tubes in the MGIT 960 and DAC systems.

3.5. DST by the Microdilution Method

The MIC of cefepime against *E. coli* was determined according to the standard CLSI guideline except for the concentration of bacteria. 16 h after culture at 37° C., broth microdilution wells were examined.

3.6. β-Lactamase Activity Analysis

A culture of *E. coli* was allowed to grow to initial Log phase (OD600=0.4). Thereafter, the bacteria were isolated from the supernatant by centrifugation at 3,000 g for 10 min. The supernatant was filtered through a 0.45-mm filter and the culture filtrate was stored. The pellets were washed twice with sterile PBS and dissolved by sonication with 60% power and 30-s pulses on ice for ≥6 min with ice. The crude lysate was centrifuged at 4° C. and 20,000 g for 30 min and the pellets were resuspended in the same volume of PBS. Each fraction corresponding to $10^7$ CFU/ml bacteria was plated in a 96-well plate for analysis. 4.5 µM Fluorocillin Green (Invitrogen) was added to each well, and the plate was gently shaken at room temperature for 5 min and cultured at 37° C. for 0.5 to 20 h. Changes in fluorescence were measured at an excitation wavelength of 485 nm and an emission wavelength of 530 nm.

3.7. Analysis of Effective Residual Concentrations of Antibiotics in Culture Media Bacterial cultures at two high or low densities were treated with each antibiotic in the liquid culture.

At each time point, the culture media were filtered to remove the cells and then added to different DST sets to measure the residual efficacies of the antibiotics. Both broth microanalysis and DAC protocol were performed in the same manner as described above.

3.8. Non-Generation of Inoculum Effect on the Standard Strain H37Rv in the DAC System and Comparison of the LJ System with the MGIT System To confirm the absence of IE in the DAC system, DST was conducted against the standard strain H37Rv at various inoculum concentrations on the DAC system. Simultaneously, DST was conducted on the LJ and MGIT systems at the same concentrations as in the DAC system. TB was used at 10-fold concentrations ($10^3$ to $10^7$). The inoculum size indicates the concentration of TB in agarose for the DAC system, the concentration of TB stock for the LJ system, and the final concentration of TB in the culture bottle for the MGIT system. Four primary drugs, rifampicin, isoniazid, ethambutol, and streptomycin, were used for DST.

In the DAC system, MIC values were the same or different by about two-fold at various inoculum concentrations (See also Table 1).

In the MGIT system, all strains were confirmed to be susceptible at $\leq 10^5$ CFU/ml but DST was impossible to measure at $10^6$ CFU/ml and $10^7$ CFU/ml because the initial inoculum concentration was excessively high. Thus, this is regarded as an error in the MGIT system. In the LJ system (MKIT), all strains were found to be susceptible at ≤$10^6$ CFU/ml but were changed to resistant at $10^7$ CFU/ml.

In conclusion, only the DAC system showed the same DST results at inoculum sizes of $10^3$ to $10^7$ CFU/ml.

3.9. Identification of the Absence of Inoculum Effect in the DAC System on Clinical Strain The standard strain H37Rv showed susceptibility to the four anti-tuberculosis drugs. Clinical strains express various phenotypes, particularly, in drug susceptibility. In order to confirm that the DAC system shows no inoculum effect on various drug susceptible strains, five clinical strains obtained from the KIT were tested at various inoculum concentrations of $10^3$ to $10^7$ CFU/ml, which is the concentration range proved to be effective in the test on the standard strain. Rifampicin, isoniazid, streptomycin, and ethambutol were used as test drugs. Actual CFU values of the clinical strains are shown in Table 6. For the 131 strains, the highest concentration was $1.3\times10^9$.

DST results obtained from the five clinical strains at $10^3$-$10^7$ CFU/ml are shown in Table 6. The three strains KHS, CMS, and CUD showed susceptibility to the three primary drugs. The DST results were the same or different by only about two-fold at $10^3$-$10^7$. Therefore, susceptibility determination was not affected by changes in inoculum concentration and all strains were found to be susceptible. The 1088 and 131 strains were resistant to the four primary drugs. All MIC values were the same irrespective of inoculum concentration. Overall, no inoculum effect on drug susceptibility was found in the DAC system.

TABLE 5

Comparison of test results for inoculum effect on the standard strain H37Rv

| | Methods | $10^7$/mL | $10^6$/mL | $10^5$/mL | $10^4$/mL | $10^3$/mL |
|---|---|---|---|---|---|---|
| INH | DAC ($10^3$, $10^4$, $10^5$), MAC2($10^6$, $10^7$) | 0.05 | 0.05 | 0.05 | 0.05 | 0.05 |
| | MGIT(0.1) | error | error | S | S | S |
| | LJ (Mkit) | R | S | S | S | S |
| RIF | DAC ($10^3$, $10^4$, $10^5$), MAC2($10^6$, $10^7$) | 0.5 | 0.5 | 0.5 | 0.5 | 0.5 |
| | MGIT(1.0) | error | error | S | S | S |
| | LJ (Mkit) | R | S | S | S | S |
| SM | DAC ($10^3$, $10^4$, $10^5$), MAC2($10^6$, $10^7$) | >2.0 | 2.0 | 2.0 | 2.0 | 2.0 |
| | MGIT(1.0) | error | error | S | S | S |
| | LJ (Mkit) | R | S | R | S | S |
| EMB | DAC ($10^3$, $10^4$, $10^5$), MAC2($10^6$, $10^7$) | 2.5 | 2.5 | 1.25 | 1.25 | 2.5 |
| | MGIT(5.0) | error | error | S | S | S |
| | LJ (Mkit) | R | S | S | S | S |

TABLE 6

Results of inoculum effect on clinical strains on the DAC system

| | Methods | $10^7$/mL | $10^6$/mL | $10^5$/mL | $10^4$/mL |
|---|---|---|---|---|---|
| MSH | | | | | |
| INH | DAC ($10^3$, $10^4$, $10^5$), MAC2($10^6$, $10^7$) | 0.025 | 0.025 | 0.025 | 0.025 |
| RIF | DAC ($10^3$, $10^4$, $10^5$), MAC2($10^6$, $10^7$) | 0.5 | 0.25 | 0.25 | 0.25 |
| SM | DAC ($10^3$, $10^4$, $10^5$), MAC2($10^6$, $10^7$) | 0.5 | 1.0 | 0.25 | 0.25 |
| EMB | DAC ($10^3$, $10^4$, $10^5$), MAC2($10^6$, $10^7$) | 1.25 | 2.5 | 2.5 | 1.25 |
| KHS | | | | | |
| INH | DAC ($10^3$, $10^4$, $10^5$), MAC2($10^6$, $10^7$) | 0.025 | 0.025 | 0.025 | 0.05 |
| RIF | DAC ($10^3$, $10^4$, $10^5$), MAC2($10^6$, $10^7$) | 0.5 | 0.25 | 0.25 | 0.25 |
| SM | DAC ($10^3$, $10^4$, $10^5$), MAC2($10^6$, $10^7$) | 1.0 | 0.5 | 0.25 | 0.5 |
| EMB | DAC ($10^3$, $10^4$, $10^5$), MAC2($10^6$, $10^7$) | 2.5 | 2.5 | 1.25 | 2.5 |
| CMS | | | | | |
| INH | DAC ($10^3$, $10^4$, $10^5$), MAC2($10^6$, $10^7$) | 0.05 | 0.025 | 0.025 | 0.05 |
| RIF | DAC ($10^3$, $10^4$, $10^5$), MAC2($10^6$, $10^7$) | 0.5 | 0.5 | 0.25 | 0.25 |
| SM | DAC ($10^3$, $10^4$, $10^5$), MAC2($10^6$, $10^7$) | 1.0 | 1.0 | 0.5 | 0.5 |
| EMB | DAC ($10^3$, $10^4$, $10^5$), MAC2($10^6$, $10^7$) | 2.5 | 2.5 | 1.25 | 1.25 |
| CYD | | | | | |
| INH | DAC ($10^3$, $10^4$, $10^5$), MAC2($10^6$, $10^7$) | 0.025 | 0.025 | 0.025 | 0.05 |
| RIF | DAC ($10^3$, $10^4$, $10^5$), MAC2($10^6$, $10^7$) | 0.5 | 0.25 | 0.25 | 0.25 |
| SM | DAC ($10^3$, $10^4$, $10^5$), MAC2($10^6$, $10^7$) | 1.0 | 0.5 | 0.25 | 0.5 |
| EMB | DAC ($10^3$, $10^4$, $10^5$), MAC2($10^6$, $10^7$) | 5.0 | 2.5 | 2.5 | 2.5 |

| | Methods | $10^7$/mL | $10^6$/mL | $10^5$/mL | $10^4$/mL | $10^3$/mL |
|---|---|---|---|---|---|---|
| 1088 | | | | | | |
| INH | DAC ($10^3$, $10^4$, $10^5$), MAC2($10^6$, $10^7$) | ≥0.2 | ≥0.2 | 0.2 | 0.2 | ≥0.2 |
| RIF | DAC ($10^3$, $10^4$, $10^5$), MAC2($10^6$, $10^7$) | ≥2.0 | ≥2.0 | ≥2.0 | ≥2.0 | ≥2.0 |
| SM | DAC ($10^3$, $10^4$, $10^5$), MAC2($10^6$, $10^7$) | ≥4.0 | ≥4.0 | ≥4.0 | ≥4.0 | ≥4.0 |
| EMB | DAC ($10^3$, $10^4$, $10^5$), MAC2($10^6$, $10^7$) | ≥10.0 | ≥10.0 | 10.0 | 10.0 | 10.0 |

TABLE 6-continued

Results of inoculum effect on clinical strains on the DAC system

131

| | | | | | | |
|---|---|---|---|---|---|---|
| INH | DAC ($10^3$, $10^4$, $10^5$), MAC2($10^6$, $10^7$) | >0.2 | >0.2 | >0.2 | >0.2 | 0.2 |
| RIF | DAC ($10^3$, $10^4$, $10^5$), MAC2($10^6$, $10^7$) | >2.0 | >2.0 | >2.0 | >2.0 | >2.0 |
| SM | DAC ($10^3$, $10^4$, $10^5$), MAC2($10^6$, $10^7$) | >4.0 | >4.0 | >4.0 | >4.0 | >4.0 |
| EMB | DAC ($10^3$, $10^4$, $10^5$), MAC2($10^6$, $10^7$) | >10.0 | >10.0 | >10.0 | >10.0 | >10.0 |

3.10. Accurate DST Requiring No Adjustment of Inoculum Size Using the DAC System An accurate inoculum amount is needed in accurate DST and MGIT, an automated liquid medium-based DST, in the LJ (Mkit) system. Thus, a troublesome procedure should be carried out to adjust the inoculum concentration.

From the previous results, it has proved that the adjustment of inoculum amounts is unnecessary in the DAC system. In this example, the adjustment of inoculum concentrations was omitted in this test and DST was directly conducted on the prepared stock solutions in the DAC system. Therefore, the inoculum amounts were used in various ranges. As shown in FIG. 10, actual inoculum concentrations were obtained by the number of colonies in 7H11 media. The inoculum concentrations were $10^5$-$10^8$ CFU/ml. DST results obtained in the DAC system were compared with those in the LJ (Mkit) system and their error rates were calculated. A total of 117 strains and a total of 516 cases were tested.

No discrepancies were noted for PanS strains that were susceptible to all drugs. In case of MDR, 8 cases were confirmed to be sensitive (major error (ME)) and 4 cases were confirmed to be resistant (very major error (VME)) in the LJ system. In a total of 516 tests, the total error rate was only 6.2%.

TABLE 7

Comparison of DST results and error rates using the LJ (Mkit) and DAC systems

| | PanS | MDR | XDR | Total |
|---|---|---|---|---|
| Total Sample | 26 | 50 | 41 | 117 |
| Total Tests | 108 | 216 | 192 | 516 |
| ME | 0 | 8 | 15 | 23 |
| VME | 0 | 4 | 2 | 6 |
| NG | 4 | 16 | 28 | 48 |
| Error Rate | 0.0% | 6.0% | 10.4% | 6.2% |

3.11. The Absence of Inoculum Effect by Wrapping of Bacteria According to the Use of Agarose Two major reasons for inoculum effect are as follows.

The first reason is that large inoculum amounts of antibiotic degrading proteins derived from bacteria may destroy antibiotics and result in an increase in MIC value. The other reason is that larger inoculum amounts of antibiotic degrading proteins derived from bacteria may decrease the number of antibiotic molecules relative to single cells of bacteria and result in an increase in MIC. To verify the reasons for the absence of inoculum effect in the DAC system, ESBL negative *E. coli* (ATCC 35218), ESBL positive *E. coli* (ATCC 25922), and clinically obtained *E. coli* strains, which are well known as a bacterial strain secreting antibiotic-degrading proteins, were tested at inoculum concentrations of $5 \times 10^7$, $5 \times 10^6$, and $5 \times 10^5$ CFU/ml. These concentrations indicate the concentrations of the bacteria in agarose for the DAC system and in liquid for the MDT system.

Cefepime, a fourth-generation cephalosporin antibiotic, was tested to demonstrate the presence of inoculum effect. The MIC ranges of the ESBL negative *E. coli* and ESBL positive *E. coli* were from 0.015 to 0.12 µg/ml.

TABLE 8

Comparison of AST results from the DAC and MDT systems at various inoculum concentrations

| DAC | ESBL+ | ESBL− | #5 |
|---|---|---|---|
| 5 * 10^5 | 0.03 | 0.06 | <16 |
| 5 * 10^6 | 0.03 | 0.06 | <16 |
| 5 * 10^7 | 0.03 | 0.06 | <16 |

| MDT | ESBL+ | ESBL− | #5 strain |
|---|---|---|---|
| 5 * 10^5 | All growth | All growth | All growth |
| 5 * 10^6 | 4 | 0.03 | 64 |
| 5 * 10^7 | 0.03 | 0.03 | 16 |

In the DAC system, no inoculum effect was observed in various inoculum amounts. In contrast, in the MDT system, ESBL + and #5 strains showed gradually increasing MIC values with increasing inoculum size. These results reveal that there is no inoculum effect in the DAC system, unlike in the MDT system.

The present inventors hypothesized that the reason why the absence of inoculum effect in the DAC system may be because proteins released from bacteria are trapped by agarose and cannot degrade the antibiotic, unlike under broth culture conditions. To demonstrate the effect of this hypothesis, other tests were conducted using ESBL positive *E. coli* strains at inoculum concentrations of $5 \times 10^7$, $5 \times 10^6$, and $5 \times 10^5$ CFU/ml. These concentrations indicate the concentrations of the bacteria in all wells for the DAC system and in liquid for the MDT system.

Thus, the final concentrations of the bacteria in the DAC and MAC systems were the same. Cefepime was used in these tests. After culture overnight, the antibiotic solutions in the wells of the DAC and MDT systems was extracted and filtered to obtain the pure antibiotic. MDT using ESBL positive *E. coli* strains was conducted using the antibiotic. The results are shown in Table 9.

TABLE 9

Comparison of AST results using the DAC and MDT systems after culture in antibiotic solutions overnight

| MIC (ug/ml) | MDT | DAC |
|---|---|---|
| 5 * 10^7 | 0.25 | 0.06 |
| 5 * 10^6 | 0.125 | 0.06 |
| 5 * 10^5 | 0.03 | 0.06 |

In the DAC system, no differences in MIC value were produced in various inoculum amounts, indicating that the degradation rates were similar to the inoculum amounts. In contrast, in the MDT system, the MIC value increased with increasing inoculum amount, indicating increased degradation of the antibiotic. These results reveal that the decreased degradation of the antibiotic in the DAC system is attributed to the trapping of the bacteria in agarose.

That is, the DAC system of the present invention has the ability to control both molecular interaction and bacterial population dynamics, which are induced by excessive binding of the drug to bacteria when the cell density increases and the resulting products. The ability of the DAC system is because the bacterial population is fixed within the matrix and the medium containing each drug is supplied into the chamber in a gradient mode.

This system facilitates DST without the need to strictly limit inoculation on mycobacteria because IE is not observed when it is inoculated in an inoculum amount larger than $10^7$ mycobacteria per ml. Therefore, the DAC system enables accurate prediction of the microbiological efficacy of anti-tuberculosis drugs and is expected to effectively replace conventional approaches.

Example 4: Application of the DAC System to Antibiotic Screening

The DAC system of the present invention was applied to antibiotic screening.

Specifically, the MIC of an anti-tuberculosis drug, Q203, which is being developed by an applicant's subcontractor, was measured to confirm the susceptibility of TDR clinical strains.

The MIC of the drug against a first clinical strain from a TDR 102 patient was determined by treating the strain with 3.9, 7.8, 15.6, 31.2, 62.5, 125, 250, 500, and 1000 ng/ml of Q203 on the DAC system. Images in the DAC system are shown in FIG. 11. The images were quantified and plotted. The results are shown in FIG. 12.

The MIC of the drug against a second clinical strain from a TDR 103 patient was determined by treating the strain with Q203 in the same manner as described above. Images in the DAC system are shown in FIG. 13. The images were quantified and plotted. The results are shown in FIG. 14.

Mode for Carrying Out the Invention

Embodiments of the present invention will now be described in detail with reference to the accompanying drawings. These embodiments are provided so that this disclosure will be thorough and complete, and will fully convey the scope of the invention to those skilled in the art. Accordingly, the present invention may be embodied in many different forms and should not be construed as limited to the exemplary embodiments set forth herein. In the drawings, the dimensions, such as widths, lengths and thicknesses, of elements may be exaggerated for clarity. The drawings are explained from an observer's point of view. It will be understood that when an element is referred to as being "on" another element, it can be directly on the other element, or one or more intervening elements may also be present therebetween. Those skilled in the art will appreciate that many modifications and variations can be made without departing from the spirit of the invention. Throughout the accompanying drawings, the same reference numerals are used to designate substantially the same elements.

One aspect of the present invention provides a bioactivity testing structure including a plate body, one or more culture units 100 arranged on the plate body, and a base plate 110 under which a solid thin film is to be formed on the bottom surface of each culture unit. FIGS. 2a and 2b are perspective and plan views of a first embodiment of the testing structure according to the present invention, respectively.

Referring to FIGS. 2a and 2b, each of the culture units may have an inlet 111 formed in the base plate and through which a mixture solution of a liquid medium containing a gelling agent and a biological agent is to be introduced. Each of the culture units 100 may have one or more connection members 113 through which the base plate 110 is connected to barriers of the plate body and cut-away grooves 114 formed between the connection members. Each of the culture units may have one or more through-holes 112 formed in the base plate 110. A bioactive agent may be uniformly diffused into the solid thin film through the cut-away grooves 114 and the through-holes 112.

The thickness and width of the solid thin film are determined depending on the depth and width of the receiving recess 120. The term "thin film" used herein refers to a thin layer that has a thickness sufficient to immobilize the biological agent and to observe the single cells. For example, the thickness of the thin film may be in the range of 1 μm to 5 mm, 1 μm to 3 mm, 1 μm to 2 mm, 1 μm to 1.5 mm, 1 μm to 1 mm, 1 μm to 800 μm, 1 μm to 500 μm, 1 μm to 100 μm, 10 μm to 3 mm, 10 μm to 1 mm, 100 μm to 1 mm, 200 μm to 1 mm, or 500 μm to 1 mm, but is not particularly limited to this range. The thickness of the solid thin film may correspond to the size in the vertical direction of the solid thin film surface to be observed. Within the thickness range of the solid thin film defined above, the single cells of the biological agent immobilized in the solid thin film can be observed, the formation of colonies can be effectively observed or the colony forming units can be counted.

The width (size) of each culture unit is not limited and may vary depending on the kind and characteristics of the biological agent. Preferably, each culture unit has a size of 1-50 mm×1-50 mm, 1-30 mm×1-30 mm, 5-50 mm×5-50 mm, 5-30 mm×5-30 mm, 10-50 mm×10-50 mm, 10-30 mm×10-30 mm or 1-20 mm×1-20 mm. Most preferably, the culture unit has a size of 12 mm×12 mm.

The height of each culture unit is also not limited and may vary depending on the kinds and characteristics of the biological agent and the bioactive agent. For example, each culture unit may have a height of 1 to 50 mm, 1 to 30 mm, 5 to 30 mm or 5 to 15 mm.

There is no restriction on the size of the through-holes 112. The diameter of the through-holes 112 is typically 1 mm or less and may be, for example, 0.99 mm or less, 0.90 mm or less, 0.85 mm or less, 0.80 mm or less, 0.75 mm or less, 0.70 mm or less, 0.65 mm or less, 0.60 mm or less, 0.55 mm or less, 0.50 mm or less, 0.45 mm or less, 0.40 mm or less, 0.35 mm or less, 0.30 mm or less or 0.25 mm or less.

In one embodiment of the present invention, the mixture solution of a liquid medium containing a gelling agent and a biological agent may be solidified under the base plate to form a biological agent-immobilized solid thin film.

The liquid medium can contain about 80% or more of water or a buffer solution. The liquid medium can be solidified due to the presence of the gelling agent. As the gelling agent, there may be exemplified agar, agarose, gelatin, alginate, collagen or fibrin. The use of agar or agarose is preferred. For example, agar may be used in an amount of 0.5 to 5% by weight in the liquid medium. The liquid medium usually requires no nutrients. In some examples, however, the liquid medium may include nutrients.

Examples of suitable biological agents include viruses, bacteria, fungi, algae, protozoa, parasitic pathogens, human and mammalian cells, and biofilms. The biological agent may grow in a liquid or solid medium and the growth thereof may be affected by the kind and concentration of a external physiologically active agent.

The density of the biological agent in the mixture solution is not limited. Particularly, the present invention features in that the density of the biological agent is irrelevant to DST or diagnostic results. That is, the DAC system of the present invention shows no inoculum effect. The density of the biological agent may be in the range of $10^1$ to $10^{80}$ cfu/ml, for example, $10^{70}$ cfu/ml or less, $10^{60}$ cfu/ml or less, $10^{50}$ cfu/ml or less, $10^{40}$ cfu/ml or less, $10^{30}$ cfu/ml or less, $10^{20}$ cfu/ml or less, $10^{10}$ cfu/ml or less, $10^9$ cfu/ml or less, $10^8$ cfu/ml or less, $10^7$ cfu/ml or less, $10^6$ cfu/ml or less, $10^5$ cfu/ml or less or $10^4$ cfu/ml or less.

The mixture solution may be solidified under the base plate to form a biological agent-immobilized solid thin film. As the temperature of the liquid medium decreases, the medium is solidified, and as a result, the biological agent is less mobile. Accordingly, the immobilization facilitates a continuous observation of the mobile biological agent.

FIGS. 3a and 3b are plan and perspective views of a second embodiment of a testing structure according to the present invention, respectively.

Referring to FIGS. 3a and 3b, each of the culture units may further have an receiving recess 120 formed on top of the base plate.

The width of the receiving recess 120 is not limited and may be, preferably from 1 to 5 mm, for example, from 1 to 4.5 mm, from 1 to 4.0 mm or from 1 to 3.5 mm. The height of the receiving recess may be preferably from 1 to 3 mm, for example from 1 to 2.5 mm.

The bioactive agent may be further introduced into the culture unit. The bioactive agent may physiologically affect the biological agent and examples thereof include: drugs such as antibiotics, anticancer agents and immunosuppressive agents, nutrients, cellular secretions, signal transducers, viruses, cells, micro RNAs, proteins, antigens, antibodies, and DNA.

The bioactive agent in admixture with a liquid medium may be introduced into each culture unit. Alternatively, the bioactive agent may be introduced into the receiving recess 120. In this case, the bioactive agent may be in a freeze-dried form that is easy to transport and store.

The plate body, the culture units, and the base plate may be partially or entirely made of a transparent or translucent material. Preferably, the testing structure is a light-transmitting substrate, which is desirable in terms of optical imaging. The testing structure is not particularly limited so long as it has surface characteristics suitable for the formation of a thin film by the application of the liquid medium.

A further aspect of the present invention provides a bioactivity testing method including: providing a mixture solution of a liquid medium containing a gelling agent and a biological agent to the bottom surface of the bioactivity testing structure; solidifying the mixture solution to form a solid thin film in which the biological agent is immobilized; supplying a bioactive agent to the solid thin film and allowing the bioactive agent to diffuse into the solid thin film; and observing the individual responses of the single cells of the biological agent to the bioactive agent or observing whether the biological agent forms colonies or the colony forming units (CFU).

The method may further include imaging the individual responses of the single cells of the biological agent to the bioactive agent, the colonies of the biological agent or the colony forming units (CFU), and analyzing the images. More preferably, the method further includes determining the minimum inhibitory concentration (MIC) of the bioactive agent based on the analysis of the images.

An optical measurement system may be used for observation. The optical measurement system may include an imaging system, such as a CCD or CMOS camera. The optical measurement system may include optical units or devices necessary for focusing and light imaging, such as a lens, an illuminator, and a light guide. The optical measurement system may include an image processing system for processing and analyzing image data observed by the imaging system. The optical measurement system rapidly records and analyzes changes in the growth of the biological agent observed during testing to obtain test results.

The bioactivity testing method may be utilized in various applications, including antibiotic susceptibility testing of bacteria, antibiotic screening, and diagnosis of bacteria.

Another aspect of the present invention provides an antibiotic screening method including: providing a mixture solution of a liquid medium containing a gelling agent and a bacterial strain to the bottom surface of the bioactivity testing structure; solidifying the mixture solution to form a solid thin film in which the bacterial strain is immobilized; supplying an antibiotic to the solid thin film and allowing the antibiotic to diffuse into the solid thin film; and observing the individual responses of the single cells of the bacterial strain to the antibiotic or observing whether the bacterial strain forms colonies or the colony forming units (CFU).

The method may further include imaging the individual responses of the single cells, the colonies or the colony forming units (CFU), analyzing the images, and determining the minimum inhibitory concentration (MIC) of the antibiotic based on the analysis of the images.

Another aspect of the present invention provides a bacterial diagnostic method including: providing a mixture solution of a liquid medium containing a gelling agent and a bacterial strain to the bottom surface of the bioactivity testing structure; solidifying the mixture solution to form a solid thin film in which the bacterial strain is immobilized; supplying a culture medium of the bacterial strain to the solid thin film and allowing the culture medium to diffuse into the solid thin film; and observing the individual responses of the single cells of the bacterial strain or observing whether the bacterial strain forms colonies or the colony forming units (CFU).

The culture medium of the bacterial strain may be further supplemented with an antibiotic and the diagnostic method may be carried out simultaneously with drug susceptibility testing.

The bioactivity testing may be drug susceptibility, drug screening or bacterial culture diagnosis testing.

There is no restriction on the kind of the bacterial strain. Most preferably, the bacterial strain is *Mycobacterium tuberculosis* or a nontuberculous *mycobacterium* (NTM). The *Mycobacterium tuberculosis* may be multi-drug-resistant (MDR) tuberculosis, extensively drug-resistant (XDR) tuberculosis or totally drug-resistant (TDR) tuberculosis.

Yet another aspect of the present invention provides a bioactivity testing system including: the bioactivity testing structure including culture units in which a bioactive agent is provided and a base plate under which a mixture solution of a liquid medium containing a gelling agent and a biological agent is solidified to form a thin film on the bottom surface of each culture unit; a stage for supporting and observing the testing structure; and a measurement system for imaging the individual responses of the single cells of the biological agent or the formation of colonies of the biological agent when the bioactive agent is delivered by diffusion or imaging the colony forming units (CFU), analyzing the images, and determining the minimum inhibitory concentration (MIC) of the bioactive agent based on the analysis of the images.

The measurement system may include an imaging system and an image processing system. The imaging system may be a CCD or CMOS camera. The image processing system is adapted to process and analyze image data observed by the imaging system.

| Explanation of Reference Numerals | |
|---|---|
| 100: Culture unit | 120: Receiving recess |
| 110: Base plate | |
| 111: Inlet | |
| 112: Through-holes | |
| 113: Connection members | |
| 114: Cut-away grooves | |

The invention claimed is:

1. A bioactivity testing structure comprising:
a plate body,
one or more culture units arranged on the plate body, and
a base plate,
wherein each of the culture units has one or more connection members through which the base plate is connected to barriers of the plate body and cut-away grooves formed between the connection members, and
the each of the culture units comprises side walls, a bottom plate, and a recess,
wherein the side walls directly contact the bottom plate, the recess is confined by the side walls and the bottom plate, and
the base plate is located in the recess of the each of the culture units and is spaced from a top surface of the bottom plate,
wherein each of the culture units has an inlet formed in the base plate and a mixture solution of a liquid medium containing a gelling agent and a biological agent is to be introduced through the inlet.

2. The bioactivity testing structure according to claim 1, wherein the bioactivity testing is drug susceptibility, drug screening, or bacterial culture diagnosis testing.

3. The bioactivity testing structure according to claim 1, wherein each of the culture units further has a receiving recess formed on top of the base plate.

4. The bioactivity testing structure according to claim 1, wherein each of the culture unit has one or more through-holes formed in the base plate.

5. The bioactivity testing structure according to claim 1, wherein each of the culture units has a size of 1-50 mm×1-50 mm and a height of 1 to 50 mm.

6. The bioactivity testing structure according to claim 3, wherein the receiving recess has a width of 1 to 5 mm and a height of 1 to 3 mm.

7. The bioactivity testing structure according to claim 1, wherein the mixture solution of a liquid medium containing a gelling agent and a biological agent is solidified between a bottom surface of the base plate and the top surface of the bottom plate to form a biological agent-immobilized solid thin film.

8. The bioactivity testing structure according to claim 1, wherein the solid thin film has a thickness of 1 μm to 10 mm.

9. The bioactivity testing structure according to claim 1, wherein a density of the biological agent in the mixture solution is from $10^1$ to $10^{80}$ cfu/ml.

10. The bioactivity testing structure according to claim 1, wherein the gelling agent is selected from a group consisting of agar, agarose, gelatin, alginate, collagen, fibrin, and mixtures thereof.

11. The bioactivity testing structure according to claim 1, wherein a bioactive agent is further introduced into the culture unit.

12. The bioactivity testing structure according to claim 11, wherein the bioactive agent is introduced in a freeze-dried form into a receiving recess.

13. The bioactivity testing structure according to claim 1, wherein the plate body, the culture units, and the base plate are made of a transparent or translucent material.

14. A bioactivity testing method comprising:
providing a mixture solution of a liquid medium containing a gelling agent and a biological agent to a bottom surface of the bioactivity testing structure according to claim 1;
solidifying the mixture solution to form a solid thin film in which the biological agent is immobilized;
supplying a bioactive agent to the solid thin film and allowing the bioactive agent to diffuse into the solid thin film; and
observing individual responses of single cells of the biological agent to the bioactive agent or observing whether the biological agent forms colonies or colony forming units (CFU).

15. The bioactivity testing method according to claim 14, further comprising
imaging the individual responses of the single cells of the biological agent to the bioactive agent, the colonies of the biological agent or the colony forming units (CFU), and
analyzing images.

16. The bioactivity testing method according to claim 15, further comprising
determining a minimum inhibitory concentration (MIC) of the bioactive agent based on the analysis of the images.

17. A method for antibiotic susceptibility testing of bacteria, comprising:
providing a mixture solution of a liquid medium containing a gelling agent and a bacterial strain to a bottom surface of the bioactivity testing structure according to claim 1;
solidifying the mixture solution to form a solid thin film in which the bacterial strain is immobilized;
supplying an antibiotic to the solid thin film and allowing the antibiotic to diffuse into the solid thin film; and
observing individual responses of single cells of the bacterial strain to the antibiotic or observing whether the bacterial strain forms colonies or colony forming units (CFU).

18. The method according to claim 17, further comprising
imaging the individual responses of the single cells, the colonies or the colony forming units (CFU),
analyzing images, and
determining a minimum inhibitory concentration (MIC) of the antibiotic based on the analysis of the images.

19. The method according to claim 17, wherein the bacterial strain is *Mycobacterium tuberculosis* or a nontuberculous *mycobacterium* (NTM).

20. The method according to claim 19, wherein the *Mycobacterium tuberculosis* is multi-drug-resistant (MDR) tuberculosis, extensively drug-resistant (XDR) tuberculosis or totally drug-resistant (TDR) tuberculosis.

21. The method according to claim 17, wherein the method shows no inoculum effect.

22. An antibiotic screening method comprising:
providing a mixture solution of a liquid medium containing a gelling agent and a bacterial strain to a bottom surface of the bioactivity testing structure according to claim 1;
solidifying the mixture solution to form a solid thin film in which the bacterial strain is immobilized;
supplying an antibiotic to the solid thin film and allowing the antibiotic to diffuse into the solid thin film; and
observing individual responses of single cells of the bacterial strain to the antibiotic or observing whether the bacterial strain forms colonies or colony forming units (CFU).

23. The antibiotic screening method according to claim 22, further comprising
imaging the individual responses of the single cells, the colonies or the colony forming units (CFU),
analyzing images, and
determining a minimum inhibitory concentration (MIC) of the antibiotic based on the analysis of the images.

24. A bacterial diagnostic method comprising:
providing a mixture solution of a liquid medium containing a gelling agent and a bacterial strain to a bottom surface of the bioactivity testing structure according claim 1;
solidifying the mixture solution to form a solid thin film in which the bacterial strain is immobilized;
supplying a culture medium of the bacterial strain to the solid thin film and allowing the culture medium to diffuse into the solid thin film; and
observing individual responses of single cells of the bacterial strain or observing whether the bacterial strain forms colonies or colony forming units (CFU).

25. The bacterial diagnostic method according to claim 24, wherein the culture medium of the bacterial strain is further supplemented with an antibiotic.

26. The bacterial diagnostic method according to claim 24, wherein the diagnostic method is carried out simultaneously with drug susceptibility testing.

27. A bioactivity testing system comprising:
the bioactivity testing structure according to claim 1, which comprises culture units in which a bioactive agent is provided and a base plate under which a mixture solution of a liquid medium containing a gelling agent and a biological agent is solidified to form a thin film on a bottom surface of each culture unit; a stage for supporting and observing the bioactivity testing structure; and
a measurement system for imaging individual responses of single cells of the biological agent or the formation of colonies of the biological agent when the bioactive agent is delivered by diffusion or imaging colony forming units (CFU), analyzing images, and determining a minimum inhibitory concentration (MIC) of the bioactive agent based on the analysis of the images.

28. The bioactivity testing system according to claim 27, wherein the measurement system comprises an imaging system and an image processing system.

* * * * *